United States Patent [19]
Scott et al.

[11] Patent Number: 5,814,300
[45] Date of Patent: Sep. 29, 1998

[54] GENE-TARGETED NON-HUMAN MAMMALS DEFICIENT IN THE SOD-1 GENE

[75] Inventors: Richard W. Scott, Wallingford; Andrew G. Reaume; Eric K. Hoffman, both of West Chester, all of Pa.

[73] Assignee: Cephalon, Inc., West Chester, Pa.

[21] Appl. No.: 398,301

[22] Filed: Mar. 3, 1995

[51] Int. Cl.[6] .......................... A61K 49/00; C12N 15/09; G01N 31/00; G01N 33/15
[52] U.S. Cl. .................. 424/9.1; 800/2; 800/DIG. 1; 800/DIG. 2; 935/70
[58] Field of Search .................. 800/2, DIG. 1, 800/DIG. 2; 435/172.3, 240.2, 240.21, 320.1, 6, 7.1; 424/9.1, 9.2; 536/23.1; 935/70, 66, 34

[56] References Cited

U.S. PATENT DOCUMENTS

| | | | |
|---|---|---|---|
| 4,736,866 | 4/1988 | Leder et al. | 800/2 |
| 4,873,191 | 10/1989 | Wagner et al. | 435/172.3 |
| 5,174,986 | 12/1992 | Berns | 424/9.2 |
| 5,175,383 | 12/1992 | Leder et al. | 800/2 |
| 5,175,384 | 12/1992 | Krimpenfort et al. | 800/2 |
| 5,175,385 | 12/1992 | Wagner et al. | 800/2 |
| 5,196,335 | 3/1993 | Groner | 435/325 |
| 5,252,476 | 10/1993 | Hallewell et al. | 435/189 |

FOREIGN PATENT DOCUMENTS

WO 90/06367 11/1989 WIPO.
WO 94/19493 2/1994 WIPO.

OTHER PUBLICATIONS

Bradley et al., 1992, Biotechnology, 10: 534–539.
Huanh et al. 1993. Free Radical Biology and Medicine, 15(5):506.
Arbones et al., "Gene Targeting in Normal Somatic Cells: Inactivation of the Interferon–y Receptor in Myoblasts", *Nat. Genet.*, 6: 90–97, 1994.
Bannister et al., "Aspects of the Structure, Function, and Applications of Superoxide Dismutase", *CRC Critical Reviews in Biochemistry*, 22(2): 111–180, 1987.
Bazzett et al., "Chronic Intrastriatal Dialytic Administration of Quinolinic Acid Produces Selective Neural Degeneration", *Exp. Neurol.* 120: 177–185, 1993.
Bendetto et al., "Isolation and Analysis of the Mouse Genomic Sequence Encoding $Cu^{2+}$–$Zn^{2+}$ Superoxide Dismutase", *Gene*, 99: 191–195, 1991.
Bewley, G. C., "cDNA and Deduced Amino Acid Sequence of Murine Cu–Zn Superoxide Dismutase", *Nucleic Acids Res.*, 16:2728, 1988.
Bowling et al., "Superoxide Dismutase Activity, Oxidative Damage, and Mitochondrial Energy Metabolism in Familial and Sporadic Amyotrophic Lateral Sclerosis", *J. Neurochem.*, 61(6): 2322–2325, 1993.
Capecchi, M. R., "The New Mouse Genetics: Altering the Genome by Gene Targeting", *Trends Genet*, 5: 70–76, 1989.
Carlioz et al., "Isolation of Superoxide Dismutase Mutants in Escherichia coli: is Superoxide Dismutase Necessary for Aerobic Life?", *EMBO J.*, 5: 623–630, 1986

(List continued on next page.)

*Primary Examiner*—Brian R. Stanton
*Attorney, Agent, or Firm*—Woodcock Washburn Kurtz Mackiewicz & Norris LLP

[57] ABSTRACT

Gene-targeted heterozygous and homozygous SOD-1 null non-human mammals, methods for producing them, and methods for use are described. Deletion vectors and gene-targeted cells are also described, as are methods for producing and using the same.

4 Claims, 11 Drawing Sheets

LEVELS OF SOD PROTEIN AND ACTIVITY IN MICE HETEROZYGOUS AND HOMOZYGOUS FOR THE SOD NULL ALLELE

OTHER PUBLICATIONS

Chan et al., "Attenuation of Glutamate–Induced Neuronal Swelling and Toxicity in Transgenic Mice Overexpressing Human CuZn–Superoxide Dismutase", *Acta Neurochirurgica. Suppl.,* 51: 245–247, 1990.

Chang et al., "Genetic and Biochemical Characterization of Cu,Zn Superoxide Dismutase Mutants in *Saccharomyces Cerevisiae*", *JBC,* 266: 4417–4424, 1991.

Church et al., "Genomic Sequencing", *Proc. Natl. Acad. Sci. USA,* 81: 1991–1995, 1984.

Deng, H.X. et al., "Amyotrophic Lateral Sclerosis and Structural Defects in Cu, Zn Superoxide Dismutase", *Science* 261: 1047–1051, 1993.

Deng et al., "Reexamination of Gene Targeting Frequency as a Function of the Extent of Homology Between the Targeting Vector and the Target Locus", *Mol. Cell. Biol.,* 12: 3365–3371, 1992.

Dousset et al., "Fluorescence Analysis of Lipoprotein Peroxidation", *Methods in Enzymology, vol. 233,* pp. 459–469, 1994.

Dower, "High Efficiency Transformation of E.coli by High Voltage Electroporation", *Nucleic Acids Res.* 16: 6127–6145, 1988.

Gurney et al., "Motor Neuron Degeneration in Mice That Express a Human Cu, Zn Superoxide Dismutase Mutation", *Science,* 264: 1772–1775, 1994.

Gurney, *Science,* 266:1587, 1994.

Gutteridge, "Invited Review: Free Radicals in Disease Processes: A Compilation of Cause and Consequence", *Free Rad. Res. Comms.,* 19: 141–158, 1993.

Halliwell and Gutteridge, "Role of Free Radicals and Catalytic Metal Ions in Human Disease: An Overview", *Methods in Enzymology, vol. 186,* pp. 1–75, 1990.

Hogan et al., *Manipulating the Mouse Embryo: A Laboratory Manual,* Cold Spring Harbor Laboratory, Cold Spring Harbor, New York, 1986.

Holmes et al., "A Rapid Boiling Method for the Preparation of Bacterial Plasmids", *Anal. Biochem.* 114: 193–197, 1981.

Hooper, et al., "HPRT–Deficient (Lesch–Nyhan) Mouse Embryos Derived from Germline Colonization By Cultured Cells", *Nature,* 326:292, 1987.

Kinouchi et al., "Attenuation of Focal Cerebral Ischemic Injury in Transgenic Mice Overexpressing CuZn Superoxide Dismutase", *Proc. Natl. Acad. Sci. USA,* 88: 11158–11162, 1991.

Koller and Smithies, "Altering Genes in Animals by Gene Targeting", *Ann. Rev. Immunol.,* 10: 705–730, 1992.

Kucha, et al., *Nature,* 326:294, 1987.

Miyamoto et al., "Idebenone Attenuates Neuronal Degeneration Induced by Intrastriatal Injection of Excitotoxins", *Exp. Neurol.,* 108: 38–45, 1990.

Mullis and Faloona, "Specific Synthesis of DNA in Vitro via a Polymerase–Catalyzed Chain Reaction", *Methods in Enzymology, vol. 155,* pp. 335–350, 1987.

Nagy, et al., "Derivation of Completely Cell Culture–Derived Mice From Early–Passage Embryonic Stem Cells", *Proc. Natl. Acad. Sci. USA,* 90: 8424–8428, 1993.

Olanow, "A Radical Hypothesis for Neurodegeneration", *TINS,* 16: 439–444, 1993.

Oncea et al., "A Sensitive Spectrophotometric Method for the Determination of Superoxide Dismutase Activity in Tissue Extracts", *Int. Immunol.,* 6: 1161–1168, 1994.

Paoletti, et al. *Anal. Biochem.,* 154:536–541, 1986.

Phillips et al., "Null Mutation of Copper/Zinc Superoxide Dismutase in Drosophila Confers Hypersensitivity to Paraquat and Reduced Longevity", *Proc. Natl. Acad. Sci. USA,* 86: 2761–2765, 1989.

Przedborski et al., "Transgenic Mice with Increased Cu/Zn–Superoxide Dismutase Activity Are Resistant to N–methyl–4–phenyl–1,2,3,6–tetrahydropyridine–Induced Neurotoxicity", *J. Neurosci.,* 12: 1658–1667, 1992.

Reaume et al., "Cardiac Malformation in Neonatal Mice Lacking Connexin43", *Science, in press,* 1995.

Reznick et al., "Oxidative Damage to Proteins: Spectrophotometric Method for Carbonyl Assay", *Methods in Enzymology, vol. 233,* p. 363, 1994.

Rinchik, "Chemical Mutagenesis and Fine–Structure Functional Analysis of the Mouse Genome", *Trends Genet.,* 7: 15–21, 1991.

Ripps et al., "Transgenic Mice Expressing an Altered Murine Superoxide Dismutase Gene Provide an Animal Model of Amyotrophic Lateral Sclerosis", *Proc. Natl. Acad. Sci. USA,* 92: 689–693, 1995.

Robertson et al., "Use of Embryonic Stem Cells to Study Mutations Affecting Postimplantation Development in the Mouse", *Ciba Found Symp.,* 165: 237–250, 1992.

Rosen et al., "Mutations in Cu/Zn Superoxide Dismutase Gene are Associated with Familial Amyotrophic Lateral Sclerosis", *Nature,* 362: 59–62, 1993.

Rothstein et al., "Chronic Inhibition of Superoxide Dismutase Produces Apoptotic Death of Spinal Neurons", *Proc. Natl. Acad. Sci. USA,* 91: 4155–4159, 1994.

Sanchez–Ramos et al., "A Marker of Oxyradical–Mediated DNA Damage (8–Hydroxy–2'Deoxyguanosine) is Increased in Nigro–Striatum of Parkinson's Disease Brain", *Neurodegen.,* : 197–204, 1994.

Sanger, "DNA Sequencing with Chain–Terminating Inhibitors", *Proc. Natl. Acad. Sci. USA,* 74: 5463–5467, 1977.

Tan et al., "The Linkage of Genes for the Human Interferon–Induced Antiviral Protein and Indophenol Oxidase–B Traits to Chromosome G–21", *J. Exp. Med.,* 137: 317–330, 1973.

teRiele et al., "Highly Efficient Gene Targeting in Embryonic Stem Cells Through Homologous Recombination with Isogeneic DNA Constructs", *Proc. Natl. Acad. Sci. USA,* 89: 5128–5132, 1992.

Troy et al., "Down–Regulation of Copper/Zinc Superoxide Dismutase Causes Apoptotic Death in PC 12 Neuronal Cells", *Proc. Natl. Acad. Sci. USA,* 91: 6384–6387, 1994.

Tybulewicz, et al., "Neonatal Lethality and Lymphopenia in Mice with a Homozygous Disruption of the c–abl Proto–Oncogene", *Cell,* 65: 1153–1163, 1991.

Walsh and Cummins, "The Open–Field Test: A Critical Review", *Physcol. Bull.,* 83: 482–504, 1976.

Wood et al., "Non–Injection Methods for the Production of Embryonic Stem Cell–Embryonic Stem Cell–Embryo Chimaeras", *Nature,* 365: 87–89, 1993.

Wurst et al., *Gene Targeting vol. 126,* Edited by A. L. Joyner, IRL Press, Oxford University Press, Oxford, England, pp. 33–61, 1993.

Yan et al., Influences of Neurotrophins on Mammalian Motoneurons in Vivo, *J. Neurobiol.,* 24: 1555–1577, 1993.

Zhang et al., "Targeting Frequency for Deletion Vectors in Embryonic Stem Cells", *Mol. Cell. Biol.,* 14: 2402–2410, 1994.

FIG.1 Prototype Gene Targeting Strategy

FIG. 2 Mouse SOD-1 Genomic Clone Maps

FIG. 5 pPNTlox² Synthesis pSK18-9 Construction pSOD3'HomolTV Construction pSOD-TV Construction

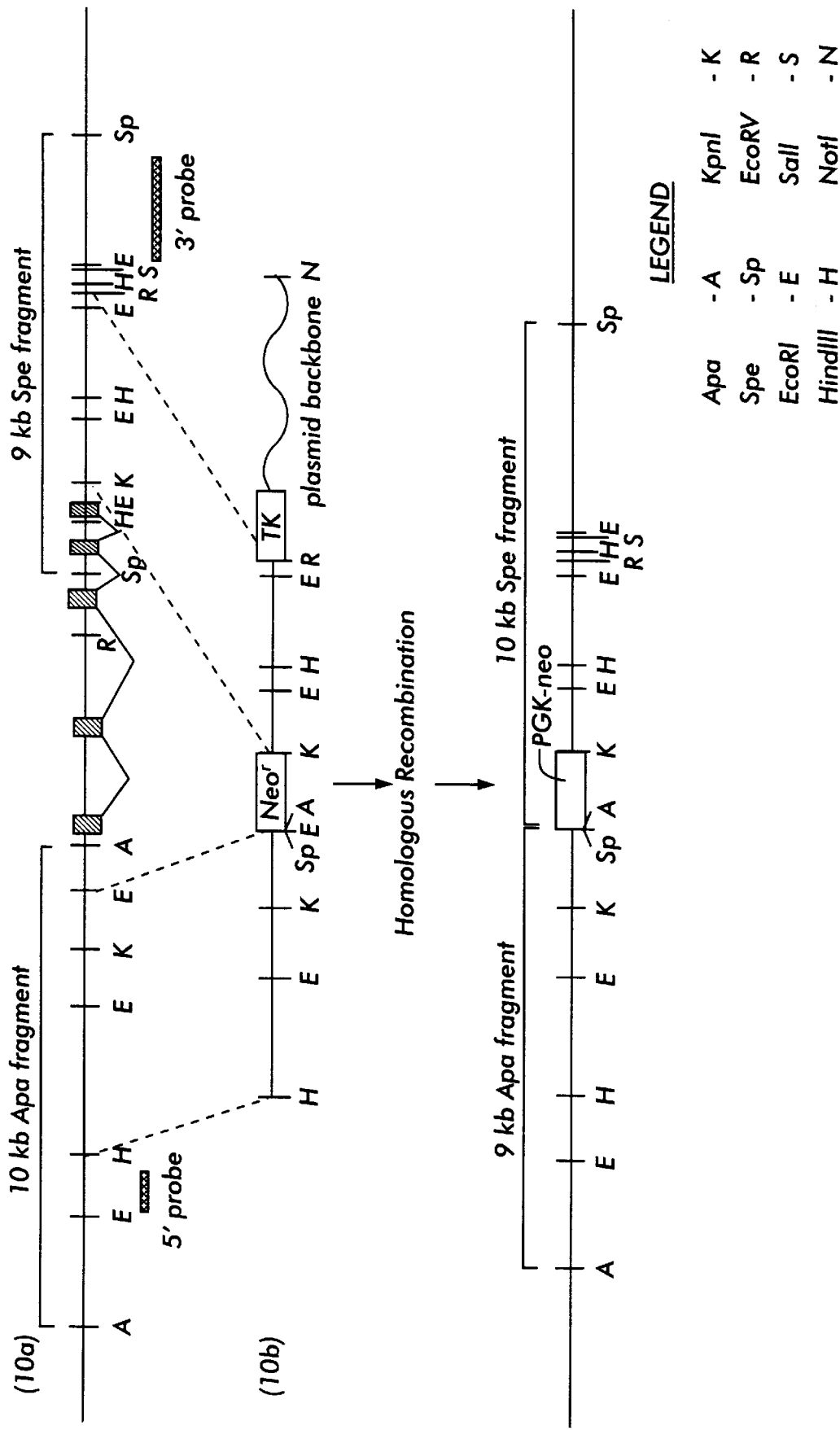

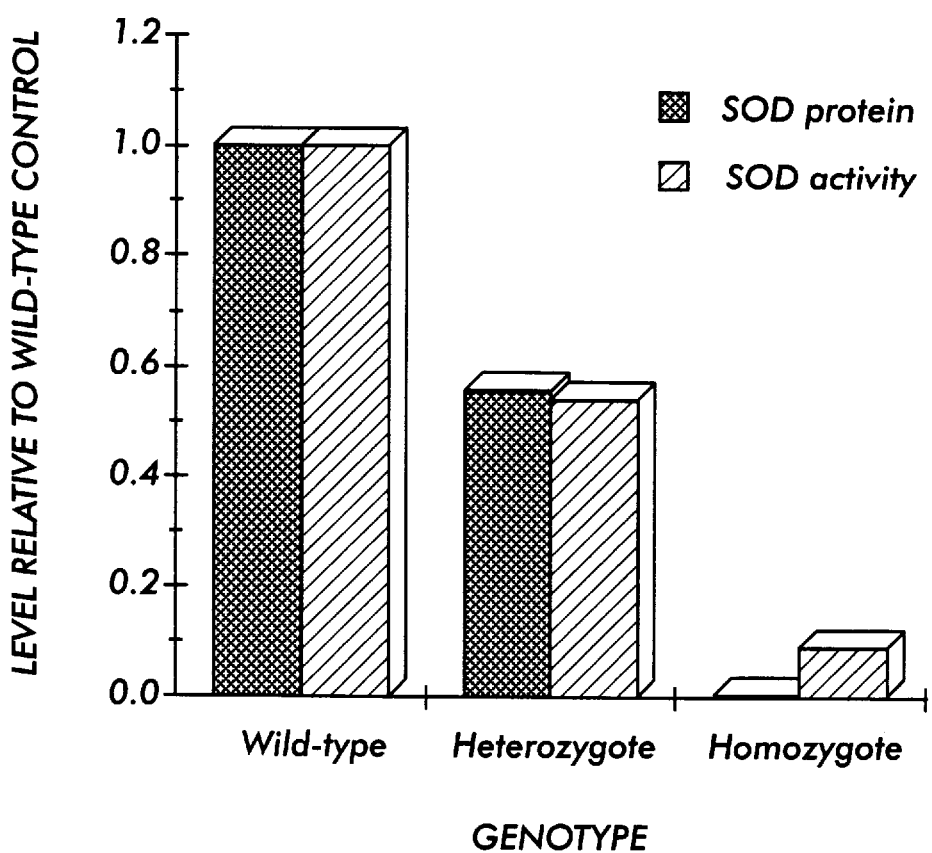
FIG. II
LEVELS OF SOD PROTEIN AND ACTIVITY IN MICE HETEROZYGOUS AND HOMOZYGOUS FOR THE SOD NULL ALLELE

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

ACCGGAATTC CATATAAGGA TATATACA 28

( 2 ) INFORMATION FOR SEQ ID NO:2:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

TAGCGAATTC AGGTTTGAAT GATCAAGT 28

( 2 ) INFORMATION FOR SEQ ID NO:3:

( i ) SEQUENCE CHARACTERISTICS:
( A ) LENGTH: 48 base pairs
( B ) TYPE: nucleic acid

```
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:3:

GGAAAGAATG  CGGCCGCTGT  CGACGTTAAC  ATGCATATAA  CTTCGTAT                    4 8

( 2 ) INFORMATION FOR SEQ ID NO:4:

( i ) SEQUENCE CHARACTERISTICS:
          ( A ) LENGTH: 47 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:4:

GCTCTCGAGA  TAACTTCGTA  TAGCATACAT  TATACGAAGT  TATATGC                     4 7

( 2 ) INFORMATION FOR SEQ ID NO:5:

( i ) SEQUENCE CHARACTERISTICS:
          ( A ) LENGTH: 33 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:5:

CGTTCTAGAA  TAACTTCGTA  TAATGTATGC  TAT                                     3 3

( 2 ) INFORMATION FOR SEQ ID NO:6:

( i ) SEQUENCE CHARACTERISTICS:
          ( A ) LENGTH: 33 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:6:

CGTGGATCCA  TAACTTCGTA  TAGCATACAT  TAT                                     3 3
```

GENE-TARGETED NON-HUMAN MAMMALS DEFICIENT IN THE SOD-1 GENE

FIELD OF THE INVENTION

This invention generally concerns gene-targeted non-human mammals; particularly, gene-targeted mice deficient in the normal SOD-1 gene; and, more particularly, gene-targeted mice deficient in the normal SOD-1 gene incapable of expressing the Cu/Zn SOD protein.

BACKGROUND OF THE INVENTION

The molecular reduction of oxygen to water during oxidative phosphorylation results inevitably in the production of superoxide radicals ("$O_2^-$") that are reactive oxygen species containing an unpaired electron orbital. Superoxides act as either reductants or oxidants and can form other reactive species including the hydroxyl radical ("$OH^-$") through interaction with iron (Haber-Weiss reaction) and peroxynitrite by reaction with nitric oxide. Reactive oxygen species attack proteins, DNA, and membrane lipids, thereby disrupting cellular function and integrity.

The primary defenses against the superoxide radicals are the superoxide dismutase enzymes (SOD) that catalyze the dismutation of superoxide to hydrogen peroxide. Three forms of SOD are known to exist in mammals: cytoplasmic SOD (Cu/Zn SOD), mitochondrial SOD (Mn SOD), and extracellular Cu/Zn SOD (EC-SOD). In mammals, SOD-1 refers to the gene that encodes Cu/Zn SOD, SOD-2 refers to the gene that encodes Mn SOD, and SOD-3 refers to the gene that encodes EC-SOD.

Cu/Zn SOD is a homodimeric protein of 32 kD that is localized to the cytoplasm and, perhaps, peroxisomes. It is produced constitutively in all cell types and is the most abundant SOD. High to moderate levels of Cu/Zn SOD are found in erythrocytes, the liver, skeletal muscle, and the brain. Mn SOD is a tetrameric protein localized to mitochondria and is found at approximately 5 to 10% of the levels of Cu/Zn SOD in cells. EC-SOD is a tetrameric protein evolutionarily related to Cu/Zn SOD that is found at low levels in plasma.

SOD-1 has been isolated and cloned from many different organisms. The complete amino acid sequences of Cu/Zn SOD from 11 different species have been compared. A high degree of homology is evident among those of vertebrate origin and the metal binding sites appear to be conserved in all the species. (Bannister et al., *CRC Critical Reviews in Biochemistry*, 22(2): 111–180, 1987, incorporated herein by reference.) The human Cu/Zn SOD has 153 amino acids per monomeric subunit and is encoded by a single-copy gene on chromosome 21. (Tan et al., *J. Exp. Med.,* 137: 317–330, 1973.) Human SOD-1 and cDNA have been cloned and sequenced. (U.S. Pat. No. 5,196,335, issued to Yoram Groner on Mar. 23, 1993; U.S. Pat. No. 5,252,476, issued to Hallewell et al. on Oct. 12, 1993, both incorporated herein by reference.) A full-length cDNA for murine Cu/Zn SOD has been isolated (Bewley, G. C., *Nucleic Acids Res.,* 16:2728, 1988, incorporated herein by reference) and the structure of the single-copy gene on chromosome 16 has been reported. (Benedetto et al., *Gene,* 99: 191–195, 1991.)

Oxidative stress has been implicated in normal aging and many human pathological conditions. (J. M. C. Gutteridge, *Free Rad. Res. Comms.,* 19: 141–158, 1993, incorporated herein by reference; Halliwell and Gutteridge, *Methods in Enzymology,* Vol. 186, pp. 1–75, 1990.) Some examples include stroke, head and spinal cord trauma, Alzheimer's disease, atherosclerosis, Parkinson's disease, and Hunting-ton's disease. Major sources of free radical production, including ischemia/reperfusion, inflammation, and mitochondrial injury, are common features of many of these conditions. Diseases in which reduced SOD activity may play a role include, for example, amyotrophic lateral sclerosis (ALS), Parkinson's disease, Fanconi's anemia and aluminum toxicity.

A detrimental role for the superoxide radical in human disease is supported in animal models of disease processes using transgenic mice overexpressing Cu/Zn SOD. Chan et al., *Acta Neurochirurgica. Suppl.,* 51: 245–247, 1990, reported that cortical neurons isolated from transgenic mice overexpressing Cu/Zn SOD two to threefold relative to normal Cu/Zn SOD levels are protected against glutamate neurotoxicity in vitro. Neuroprotection is also conferred in Cu/Zn SOD transgenic mice against focal cerebral ischemia (Kinouchi et al., *Proc. Natl. Acad. Sci. USA,* 88: 11158–11162, 1991) and N-methyl-4-phenyl-1,2,3,6-tetrahydropyridine (MPTP) induced toxicity that causes damage similar to that observed in Parkinson's disease (Przedborski et al., *J. Neurosci.,* 12: 1658–1667, 1992).

Evidence for a direct role of Cu/Zn SOD in human disease is exemplified by the disease ALS. ALS is a progressive paralytic disorder caused by the degeneration of large motor neurons of the brain and spinal cord and is usually fatal within five years of onset of symptoms. Approximately 90% of ALS is "sporadic", i.e., no familial history of the disease. Enhanced oxidative damage and stress in sporadic ALS patients, as evidenced by increases in protein carbonyl content and complex I electron transport activity, was reported by Bowling et al., *J. Neurochem.,* 61(6): 2322–2325, 1993. Approximately 10% of ALS is inherited as an autosomal dominant trait and is termed familial ALS (FALS). Recently, in a subset of FALS cases, 16 different missense mutations were identified within SOD-1 that resulted in a 40 to 50% reduction in the Cu/Zn SOD activity measured in red blood cell lysates. (Rosen et al., *Nature,* 362: 59–62, 1993; Deng, H. X. et al., *Science* 261: 1047–1051, 1993.)

The role of reduced Cu/Zn SOD activity in FALS is unclear, however, because transgenic mice overexpressing human Cu/Zn SOD bearing one of the FALS mutations develop progressive motor neuron loss similar to that observed in the human condition. (Gurney et al., *Science,* 264: 1772–1775, 1994). Ripps et al., *Proc. Natl. Acad. Sci. USA,* 92: 689–693, 1995, report that transgenic mice bearing a mutation in the mouse SOD-1 gene that corresponds to one of the changes in human FALS gene have high expression of the altered gene in the central nervous system which is associated with an age-related rapidly progressive decline of motor function accompanied by degenerative changes of motorneurons within the spinal cord, brain stem, and neocortex. The tissues of these transgenic mice had normal levels of total SOD activity. This suggests that the mutations confer a gain-of-function on the Cu/Zn SOD protein that contributes to disease onset. One possibility is that reduced Cu/Zn SOD activity measured in the FALS patients is a co-factor in the disease. (Gurney, *Science,* 266:1587, 1994.)

To determine whether decreased SOD activity could contribute to motor neuron loss, Cu/Zn SOD was inhibited chronically with antisense oligonucleotides or diethyldithiocarbamate in spinal cord organotypic cultures derived from rats. Chronic inhibition of Cu/Zn SOD resulted in the apoptotic degeneration of spinal neurons, including motor neurons. Motor neuron toxicity could be entirely prevented by the antioxidant N-acetylcysteine. (Rothstein et al., *Proc. Natl. Acad. Sci. USA,* 91: 4155–4159, 1994.) Similarly, Troy et al., *Proc. Natl. Acad. Sci. USA*, 91: 6384–6387, 1994, reported that inhibition of Cu/Zn SOD synthesis by antisense oligonucleotides in cultured PC12 cells (rat pheochromocytoma cells) results in apoptotic-like cell death in undifferentiated and nerve growth factor (NGF)-differentiated cultures. The authors suggest that free radical production caused by inhibition of Cu/Zn SOD is responsible for induction of the cell death pathway.

An animal model deficient in, or completely lacking, Cu/Zn SOD, would facilitate the elucidation of the role of Cu/Zn SOD and superoxide radicals in disease, and the testing of counteractive compounds. The development of an animal model affords both in vivo and in vitro testing opportunities as cultured cells from the SOD-1 deficient or lacking animals can be utilized for the in vitro testing. An animal model deficient in Cu/Zn SOD will permit one to determine whether there are compensatory responses of other anti-oxidant systems, including Mn SOD and EC-SOD.

It has been proposed that SOD is essential for normal aerobic life. (C. W. Olanow, *TINS*, 16: 439–444, 1993.) For example, non-mammalian SOD deficient organisms have been established which exhibit highly deleterious characteristics. *Escherichia coli* lacking SOD activity exhibit an oxygen-dependent auxotrophy for branched chain amino acids. These organisms are unable to grow aerobically on minimal media, and are highly sensitive to the free radical-producing agents paraquat and hydrogen peroxide. (Carlioz et al., *EMBO J.*, 5: 623–630, 1986.) Cu/Zn SOD deficient yeast (*Saccharomyces cerevisiae*) are intolerant to atmospheric levels of oxygen and are auxotrophic for lysine and methionine. (Chang et al., *JBC*, 266: 4417–4424, 1991.) Null mutations for Cu/Zn SOD in *Drosophila melanogaster* cause toxic hypersensitivities to oxidative stress conditions and a significant reduction in the adult lifespan. (Phillips et al., *Proc. Natl. Acad. Sci. USA*, 86: 2761–2765, 1989.)

SUMMARY OF THE INVENTION

In one aspect, the present invention relates to heterozygous SOD-1 null non-human mammals, preferably exemplified by a gene-targeted mouse lacking one normal copy (allele) of SOD-1, thereby producing a reduced amount of Cu/Zn SOD. In a preferred aspect, the invention relates to homozygous SOD-1 null non-human mammals exemplified by a gene-targeted mouse lacking both normal copies (alleles) of SOD-1, thereby producing no measurable amount of Cu/Zn SOD protein.

In another aspect, the present invention relates to a recombinant DNA construct for effecting the gene targeting by means of homologous recombination.

In yet another aspect, the present invention relates to methods for testing the effectiveness of compounds in counteracting the effects of oxidative stress.

In a further aspect, the present invention relates to gene-targeted cells lacking at least one normal SOD-1 allele.

BRIEF DESCRIPTION OF THE DRAWINGS

FIGS. 10a and 10b depict the strategy used to detect homologous recombination within mouse SOD-1.

FIG. 11 depicts the measurement of Cu/Zn SOD concentration and activity levels in blood samples from wild-type mice, and mice heterozygous and homozygous for the SOD-1 null allele.

DETAILED DESCRIPTION

Figure 1:
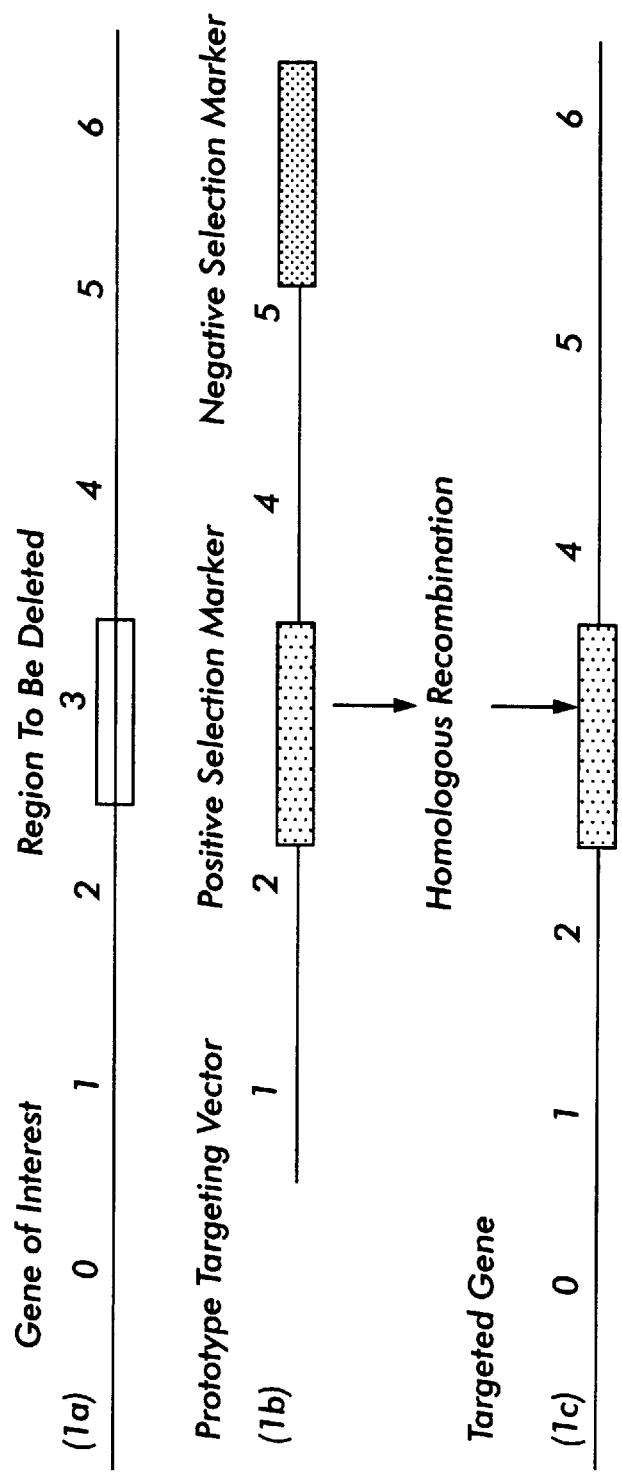
FIGS. 1a, 1b, and 1c depict a prototype gene targeting strategy.

Because SOD is the initial defense against oxygen toxicity, and cytoplasmic Cu/Zn SOD represents a large fraction of SOD activity in mammals, it was not predictable whether mammals completely lacking Cu/Zn SOD, i.e., null for both alleles, could survive. With the advent of methods for introducing gene-targeted mutations in mammals currently exemplified in the art using mice, it was of interest to determine whether ablation or "knock-out" of the mouse normal SOD-1 gene could be accomplished resulting in gene-targeted, non-human mammals deficient in or lacking cytoplasmic Cu/Zn SOD activity, and whether mammals lacking Cu/Zn SOD activity would be able to survive. Such mutagenized mammals are useful for directly addressing the role of oxidative stress in any number of pathological conditions—i.e., aging, radiation damage, immunological dysfunction, and neurological disorders—in which free radical damage has been implicated.

As disclosed in more detail below, gene-targeted mammals according to the invention lacking one normal copy of SOD-1 (or SOD-1 allele) produce a reduced amount of Cu/Zn SOD. Such mammals are defined herein as "deficient" in SOD-1, and are termed "heterozygous SOD-1 null." Mammals according to the invention lacking both copies of normal SOD-1 produce substantially no, or no measurable amount, of Cu/Zn SOD. Such mammals are defined herein as "lacking" SOD-1, and are termed "homozygous SOD-1 null."

As used herein, the phrase "normal" or "normal copy" in reference to SOD-1 or SOD-1 allele means the gene encoding wild type amounts of enzymatically active Cu/Zn SOD protein in a wild type mammal whose genome includes such SOD-1. Thus, an animal lacking at least one normal copy of an allele, as defined herein, need not necessarily have that allele excised form the genome of that animal; rather, the gene sequence can be sufficiently disrupted such that the expression of a protein encoded thereby is disrupted. Therefore, a mammal lacking at least one copy of a normal SOD-1 allele can, as defined herein, have a mutated SOD-1 allele that disrupts expression of the Cu/Zn SOD.

As used herein, the term "reduced amount" in reference to the amount of Cu/Zn SOD protein expressed in a gene-targeted mammal lacking one normal copy of SOD-1 gene means between about 25% and about 75% of wild-type Cu/Zn SOD protein typically expressed in a comparative mammal (e.g., a mouse in the case of the gene-targeted mouse).

As used herein, the term "no measurable amount" in reference to the amount of Cu/Zn SOD protein expressed in a gene-targeted mammal lacking both copies of normal SOD-1 means less than about 10% of wild-type Cu/ZN SOD protein normally expressed in a comparative mammal.

Methodologies for measurement of protein expressed by a gene are varied and well-known; analyses may be made, for example, using anti-Cu/Zn SOD protein antibody measurements of tissue samples such as exemplified in Example 5 below.

As used herein, the term "about" in reference to a numerical value means "±10%" of the numerical value, e.g., "about 10%" means between 9% and 11%.

As used herein, the term "control" is given the definition ordinarily ascribed to the word in a scientific setting; thus, in situations where a putative therapeutic compound is provided to, e.g., a homozygous SOD-1 null mouse, to determine the effectiveness of the compound for counteracting the deleterious effects of oxidative stress, a "control" for such an analysis could be, e.g., a homozygous SOD-1 null mouse that is not provided with the compound; a SOD-1 null mammalian cell that is not provided with the compound, etc.

To implicate oxidative stress as an etiological factor in human neurological disease, deficits that develop spontaneously in specific neuronal populations vulnerable to disease can be evaluated during normal aging. Examples of some deficits include the accumulation of oxidative damage on protein and enzymes (Reznick et al., *Methods in Enzymolology*, Vol. 233, p. 363, 1994; Bowling et al., supra), DNA (Sanchez-Ramos et al., *Neurodegen.*, 3: 197–204, 1994) and membrane lipids (Doussut et al., *Methods in Enzymolology*, Vol. 244, pp. 459–469, 1994). Additional deficits include neuronal cell loss and behavioral abnormalities (Walsh and Cummins, *Physcol. Bull.*, 83: 482–504, 1976). More specifically, the influence of oxidative stress on apoptotic cell death in vivo can be examined in the SOD-1 deficient and SOD-1 lacking mammals during normal aging or after pharmacological lesions of particular neuronal populations. Apoptosis is established by measuring DNA cleavage, nuclear condensation, and cellular morphology (Rothstein et al., *Proc. Natl. Acad. Sci. USA*, 91: 4155–4159, 1994). Pharmacological lesions of interest include excitotoxicity (Miyamoto et al., *Exp. Neurol.*, 108: 38–45, 1990; Bazzett et al., *Exp. Neurol.* 120: 177–185, 1993), focal ischemia (Kinouchi et al., *Proc. Natl. Acad. Sci. USA*, 88: 11158–11162, 1991) and facial motor neuron axotomy (Yan et al., *J. Neurobiol.*, 24: 1555–1577, 1993).

Having established viable gene-targeted mammals which are both heterozygous SOD-1 null and homozygous SOD-1 null, analysis of the effects of having a reduced amount of Cu/Zn SOD protein, and no measurable amount of Cu/Zn SOD protein, respectively, on the development and behavior of such mammals can be determined. Oxidative stress can be potentiated by providing the heterozygotes and homozygotes a vitamin E/selenium deficient diet, exercise, and/or exposure to hyperbaric oxygen. Putative therapeutic agents for countering the effects of a Cu/Zn SOD deficiency can be analyzed and screened. Furthermore, the mammals can be used as a source of cells for culture for in vitro testing. Those skilled in the art will readily recognize the myriad of available choices for positive utilization of such mammals.

Administration of the compound to be tested may be carried out by any appropriate means. In the case of the gene-targeted mammals, for example, administration may be intracerebrally and/or intracerebroventricularly, and/or intravascularly, intralymphatically, parenterally, subcutaneously, intramuscularly, intraperitoneally, intrastitially, hyperbarically, and the like, using a variety of dosage forms and amounts, the particular route of administration and the dosage form and amount being dependent on various factors such as the type of compound being tested, the age, weight, and type of mammal model etc. In the case of the gene-targeted cells, administration of the compound to be tested may be carried out, if desired, by simply placing the compound in the cell culture medium. Generally, a lower dosage amount will be employed with the gene-targeted cells than with the gene-targeted mammals.

Deletion of the SOD-1 gene in a mouse genome is specifically disclosed below. Currently, gene-targeting protocols utilized in the art are defined by the mouse; however, as the state of the gene-targeting art progresses to other mammals (i.e., rats, pigs, rabbits, non-human primates), the technique and methods disclosed below can rapidly be adapted thereto.

The deletion of SOD-1 was accomplished by first effecting the deletion of SOD-1 in embryonic stem (ES) cells using homologous recombination, resulting in mutagenized ES cells. The SOD-1 deletion was then incorporated into a mouse by introducing the mutagenized ES cells into a developing mouse embryo. Breeding the resulting chimeric mice and their progeny produced some mice which were lacking one normal copy of SOD-1 (heterozygotes) and others which were lacking both normal copies (homozygotes).

Although we disclose herein our most preferred strategy for the development of heterozygous SOD-1 null non-human mammals and homozygous SOD-1 null non-human mammals using a most preferred gene-targeting vector ("deletion vector"), other strategies and targeting vectors will be readily apparent to those skilled in the art. Thus, the following disclosure is neither intended to be, nor to be construed as, a limitation on the disclosure or the claims to follow.

FIG. 1 depicts a general paradigm for introducing deletions into a mammalian genome using homologous recombination, as has been reviewed by Capecchi, M. R., *Trends Genet,* 5: 70–76, 1989 and Koller and Smithies, *Ann. Rev. Immunol.,* 10: 705–730, 1992, both incorporated herein by reference. However, other methods can be utilized for mutagenizing the mammalian genome. These include other methods of gene-targeting (for examples, see Capecchi, supra; Koeller and Smithies, supra) chemical mutagenesis (Rinchik, *Trends Genet.,* 7: 15–21, 1991) and insertional inactivation of genes by the random integration of vectors such as retroviruses (Robertson et al., Ciba Found Symp., 165: 237–250, 1992).

A length of genomic DNA is first depicted by organizing it into regions (numbered 0–6 in FIG. 1a). In FIG. 1, region 3 is designated to be deleted. Homologous recombination using a gene-targeting vector is utilized. The type of gene-targeting vector used for the deletion of a gene is termed a replacement or deletion vector.

"Deletion vector" as used herein refers to a vector that includes one or more selectable marker sequences and two sequences of DNA homologous to the genomic DNA that flank the DNA gene sequence which is to be deleted. An "homologous sequence" as used herein is defined as a sequence at least about 90%, but preferably about 95%, identical to the corresponding target sequence. These flanking sequences are termed "arms of homology." In FIG. 1b, the arms of homology are represented by regions 1–2 and 4–5. Preferably, these arms of homology are substantially isogenic for the corresponding flanking sequences in the cell being targeted or "target cell." A "substantially isogenic" sequence is at least about 97–98% identical to the corresponding target sequence. The use of DNA isogenic to the target cells helps assure high efficiency of recombination with the target sequences. (teRiele et al., *Proc. Natl. Acad. Sci. USA*, 89: 5128–5132, 1992.) The cumulative region of homology is longer than about 50 bp but is preferably about 2 kb or greater.

The deletion vector preferably includes at least a positive selection marker within the arms of homology to enable the scoring of recombination. Such positive selection markers can confer a phenotype not normally exhibited by wild-type mammals; for example, resistance to a substance normally toxic to the target cell. In this example, the positive selection marker can be flanked by loxP sites allowing for excision of the positive selection marker; see, for example, U.S. Pat. No. 4,959,317, issued to B. L. Sauer on Sep. 29, 1990, incorporated herein by reference. In a further preferred embodiment, the deletion vector also includes one or more negative selection markers outside the arms of homology to facilitate identification of proper homologous recombinants. The negative selection markers can confer, for example, sensitivity to a substance not normally toxic to the target cell. The selection markers can be gene cassettes—ie., include both a promoter and an accompanying coding sequence. The result of homologous recombination of the gene-targeting vector with cellular DNA in the paradigm is shown in FIG. 1c. As depicted therein, region 3 has been replaced by the positive selection marker.

In the specific deletion vector according to the present invention, the positive selection marker is $neo^r$, a gene that encodes resistance to the neomycin analog G418, and the negative selection marker is the herpes simplex virus thymidine kinase gene (HSV-TK), a gene that encodes susceptibility to ganciclovir. Upon successful gene-targeting and homologous recombination, the positive selection marker is incorporated into the genome in place of the gene to be deleted within the arms of homology, thereby making the gene-targeted cells resistant to G418, while the negative selection marker is excluded, thereby maintaining the cells' resistance to ganciclovir. Thus, to enrich for homologous recombinants, gene-targeted cells are grown in culture medium containing G418 to select for the presence of the $neo^r$ gene, and ganciclovir to select for the absence of the HSV-TK gene.

The "target cells" are those cells to be mutagenized. The target cells specifically disclosed herein are mouse embryonic stem cells. However, other cells can be utilized. The "gene-targeted cells" are those cells which are mutagenized. Gene-targeted cells lacking at least one normal copy of SOD-1 allele can be utilized in the generation of gene-targeted mice, for example. The gene-targeted cells which lack at least one normal SOD-1 allele can be utilized, for example, in high through-put screening of agents such as superoxide scavenging compounds. Such "screening cells" can be cryopreserved until utilized for such screening. See, for example, Oncea et al., *Int. Immunol.*, 6: 1161–1168, 1994 and Arbones et al., *Nat. Genet.*, 6: 90–97, 1994.

The specific procedure followed is detailed below. The following restriction enzymes, and their single letter codes, are referred to in the examples which follow: EcoRI (E), HindIII (H), KpnI (K), EcoRV (R), SalI (S) and NotI (N).

EXAMPLE 1

Cloning of Mouse SOD-1

Figure 2:
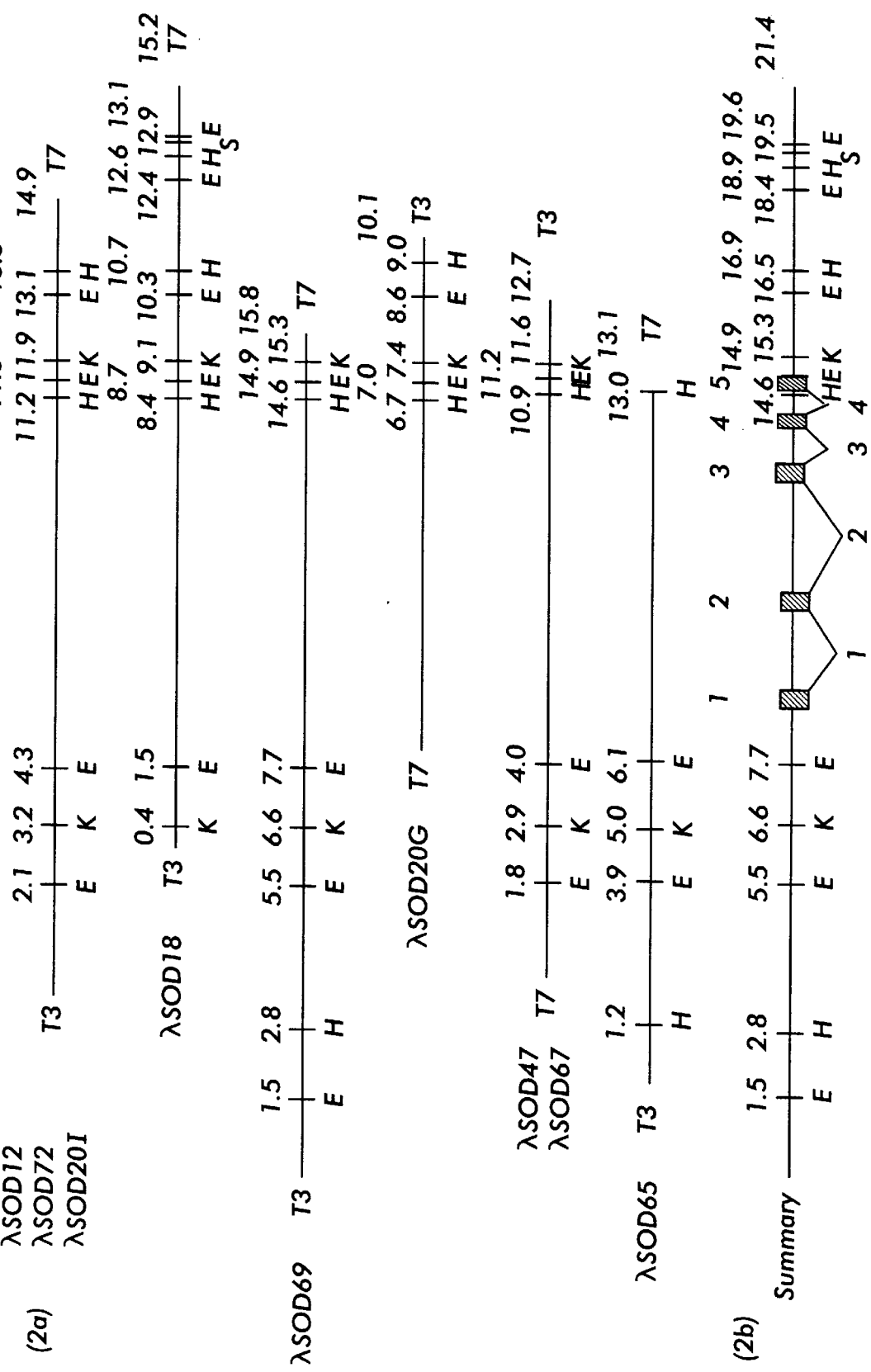
FIGS. 2a and 2b depict mouse SOD-1 genomic clone maps (2a) and a composite determined therefrom (2b).

The mouse SOD-1 genomic DNA was cloned from a phage library created from 129/Sv mouse DNA partially digested with Sau3A and inserted into the BamHI site of Lambda DASH® II (Reaume et al., *Science*, in press, 1995). Using standard molecular biology techniques (Maniatis et al., *Molecular Cloning: A Laboratory Manual*, Cold Spring Harbor Laboratory, Cold Spring Harbor, N.Y., 1982) approximately $1.2 \times 10^6$ recombinant bacteriophages were screened for the presence of SOD-1 sequences by hybridization with a 900 base pair (bp), radiolabelled SOD-1 intron-specific DNA probe. This 900 bp probe was generated by polymerase chain reaction (PCR) amplification (Mullis and Faloona, *Methods in Enzymolology*, Vol. 155, pp. 335–350, 1987, incorporated herein by reference) of mouse genomic DNA using primers EH100 (ACC GGA ATT CCA TAT AAG GAT ATA TAC A; SEQ ID NO:1) and EH101 (TAG CGA ATT CAG GTT TGA ATG ATC AAG T; SEQ ID NO:2) which hybridize to each end of the SOD-1 intron 4 (FIG. 2b). The approximate placement of the 5 SOD-1 exons is shown in FIG. 2b as based on data from Bendetto et al., *Gene*, 99: 191–195, 1991, incorporated herein by reference, and marked above the map with bold numbers. The corresponding introns are numbered below the map in bold italics.

The amplified fragment was separated from the other components of the reaction by electrophoresis on a 1.0% agarose gel, and purified using GeneClean® II (Bio 101, Inc., La Jolla, Calif.). Purified probe DNA was radioactively labelled with $^{32}$P-dCTP by the random primer method using materials and methods supplied by the kit manufacturer (Multiprime DNA Labeling System; Amersham Life Sciences, Arlington Heights, Ill.).

From this screen, 9 clones were identified which hybridized to the SOD-1 intron probe: λSOD12, λSOD72, λSOD20I, λSOD18, λSOD69, λSOD20G, λSOD47, λSOD67, and λSOD65 (FIG. 2a). These clones were purified by limiting dilution and plaque hybridization with the SOD-1 intron 4 probe (Maniatis et al., 1982, supra).

Figure 3:
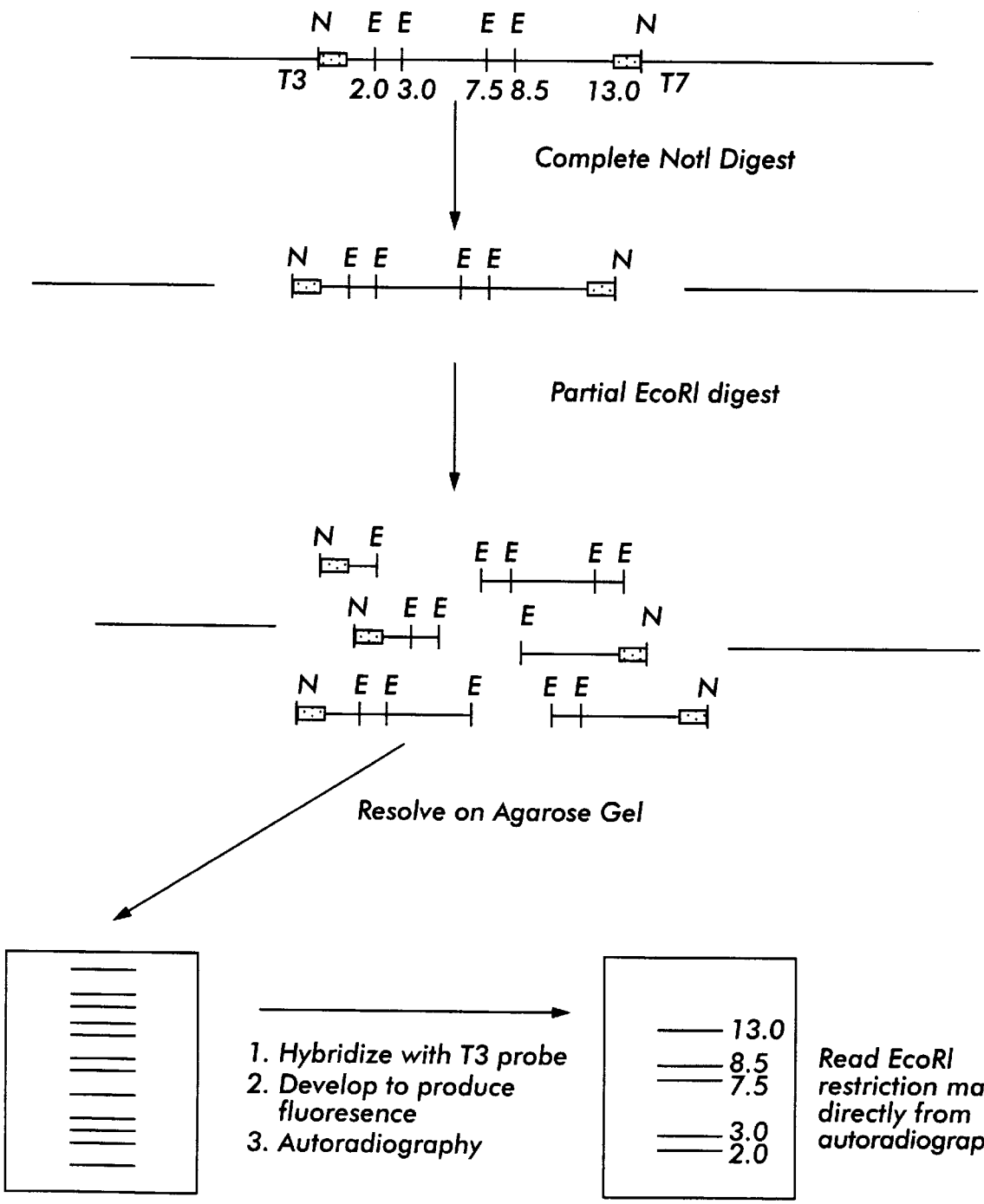
FIG. 3 depicts restriction mapping with the FLASH® Nonradioactive Gene Mapping Kit. A typical restriction map for a genomic clone isolated from a Lambda DASH® II library is shown at the top of the figure.

For each clone, DNA was prepared from bacteriophage particles first purified on a CsCl gradient (Maniatis et al., 1982, supra). Restriction maps were then generated for each of the cloned inserts using the FLASH® Nonradioactive Gene Mapping Kit (Stratagene® Inc., La Jolla, Calif.), as summarized in FIG. 3. This method of restriction enzyme mapping involves first completely digesting 10 μg of the phage DNA with the restriction enzyme NotI using standard restriction enzyme digest conditions (Maniatis et al., 1982, supra). NotI cuts all clones in the vector DNA at either end of the cloned insert, leaving a T3 bacteriophage promoter attached to one end of the insert and a T7 bacteriophage promoter attached to the other end. The NotI digested DNA was then partially digested with the enzyme EcoRI, as an example, using limiting amounts of enzyme (0.2 units/μg DNA), in an 84 μl reaction volume at 37° C. Aliquots (26 μl) were removed after 3 minutes, 12 minutes, and 40 minutes and the digest reaction was stopped by the addition of 1 μl of 0.5M EDTA. DNA from all three time points was resolved on a 0.7% agarose gel, visualized by ethidium bromide staining, and then transferred to a GeneScreen Plus® membrane (NEN® Research Products, Boston, Mass.) by capillary transfer (Maniatis et al., 1982, supra). The membrane was hybridized with an alkaline phosphatase labelled oligonucleotide that was specific for the T3 promoter (supplied with the FLASH® kit) using reagents and methods supplied by the kit manufacturer. After hybridization, the membrane was washed and developed with a chemiluminescent-yielding substrate and then exposed to X-ray film in the dark for approximately 60 minutes.

The oligonucleotide probes effectively label one end of the insert. By determining the positions of the bands on the X-ray film and calculating the DNA size to which they correspond, it was possible to determine the position of the EcoRI sites relative to the T3 end of the insert. These results were then complemented by stripping the probe off of the membrane, and rehybridizing with a T7-specific oligonucleotide in order to determine the positions of the EcoRI sites relative to the T7 end of the insert. This process was repeated using the enzymes HindIII and KpnI.

The results of restriction mapping of the 9 different SOD genomic clones using the FLASH® Nonradioactive Gene Mapping Kit (Stratagene® Inc., La Jolla, Calif.) are depicted in FIG. 2a. Some clones were isolated multiple times and therefore have more than one name. By comparing the restriction enzyme maps of the different overlapping clones, a composite map was assembled (FIG. 2b). Of the 9 original clones isolated, a total of six independent clones were identified.

EXAMPLE 2

Construction of a Deletion Vector

Figure 4:
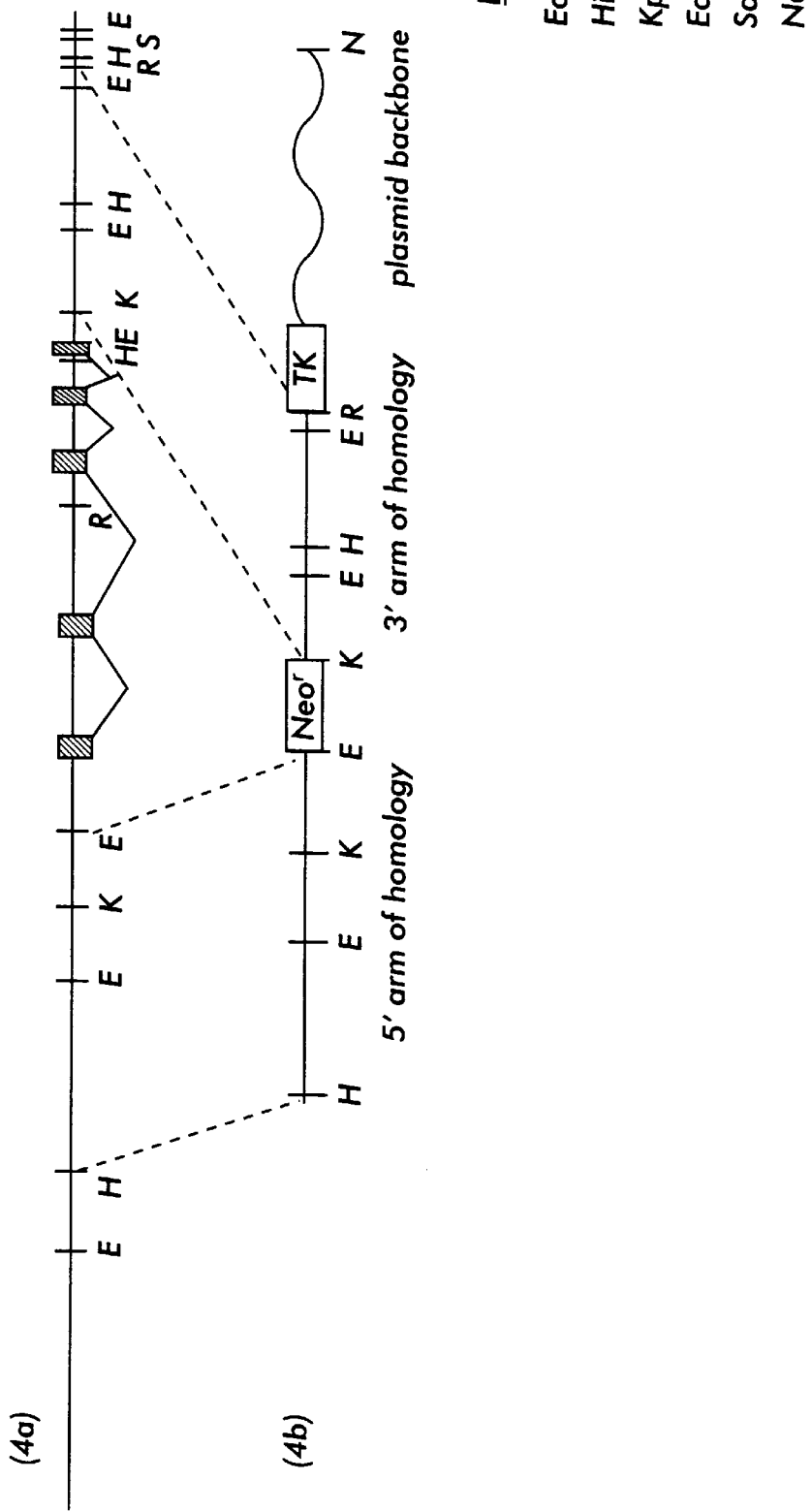
FIGS. 4a and 4b depict the SOD genomic map (4a) and targeting vector (4b).

Examination of the published report that describes the structure of the mouse SOD-1 gene (Bendetto, et al., supra), revealed that the entire coding sequence of the mouse SOD-1 gene is within a 7.2 kb EcoRI fragment of DNA (FIG. 2b). Based on available restriction site data and preferred sizes for arms of homology (Deng et al., *Mol. Cell. Biol.,* 12: 3365–3371, 1992; Zhang et al., *Mol. Cell. Biol.,* 14: 2402–2410, 1994), a 4.9 kb HindIII-EcoRI fragment was selected for the 5'-arm of homology and a 3.3 kb KpnI-EcoRV fragment was selected for the 3' arm (FIG. 4a). A targeting vector was created by isolating these two fragments and placing them into a plasmid which contained a $neo^r$ cassette (a neomycin phosphotransferase gene linked to a phosphoglycerate kinase promoter) as a positive selection marker, a TK cassette (a Herpes simplex virus thymidine kinase gene linked to a phosphoglycerate kinase promoter) as a negative selection marker, and linker sequences, to produce the deletion vector pSOD-TV. The process is set forth in detail below.

Figure 5:
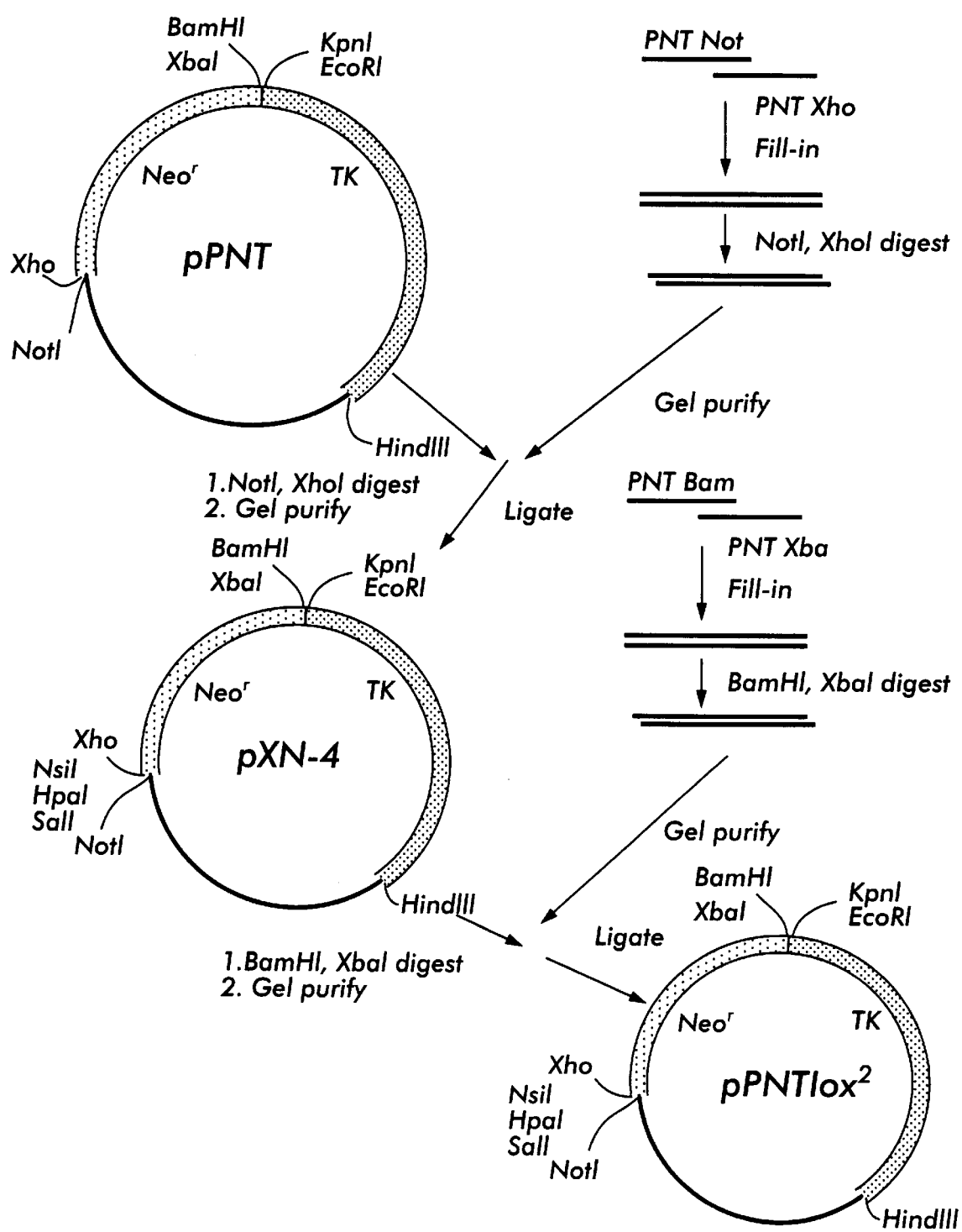
FIG. 5 depicts the construction of intermediate plasmid pPNTlox$^2$.

Construction of the Intermediate Plasmid pPNTlox$^2$ pSOD-TV was created from a derivative of pPNT (Tybulewicz, et al., *Cell,* 65: 1153–1163, 1991, incorporated herein by reference; obtained from Dr. Richard Mulligan, MIT, Cambridge, Mass.) by first inserting two oligonucleotide linkers on each side of the $neo^r$ cassette creating the intermediate plasmid pPNTlox$^2$ (FIG. 5). A double-stranded 79 base pair 5' linker having SalI, HpaI, and NsiI sites was created by annealing two single-stranded oligonucleotides that overlap at their 3' ends and then filling in the remaining single-stranded regions with the Klenow fragment of DNA polymerase I. The oligonucleotides PNT Not (GGA AAG AAT GCG GCC GCT GTC GAC GTT AAC ATG CAT ATA ACT TCG TAT; SEQ ID NO:3) and PNT Xho (GCT CTC GAG ATA ACT TCG TAT AGC ATA CAT TAT ACG AAG TTA TAT GC; SEQ ID NO:4) (150 ng of each) were combined in a 30 μl reaction mixture containing 5 U of Klenow polymerase, Klenow polymerase buffer, and 2 mM dNTPs (dATP, dCTP, dGTP, and dTTP). After incubating for 1 hour at 37° C., a portion (5 μl) of this reaction mixture was simultaneously digested with the restriction enzymes NotI and XhoI to liberate the restriction enzyme sites at each end of the linker. In addition, 200 ng of pPNT was digested with NotI and XhoI. The digested plasmid was resolved on a 0.8% agarose gel, purified from the gel, and treated with calf intestinal phosphatase according to standard methods (Maniatis et al., 1982, supra) . A quantity (66 ng) of the double digested linker was ligated to the double digested and phosphatase-treated PPNT DNA (Maniatis et al., 1982, supra). Following DNA transformation of competent WM1100 *E. coli* (Dower, *Nucleic Acids Res.* 16: 6127–6145, 1988, incorporated herein by reference), plasmid DNA was isolated from ampicillin-resistant bacteria (Holmes et al., *Anal. Biochem.* 114: 193–197, 1981, incorporated herein by reference) and analyzed by restriction enzyme analysis. The proper recombinant plasmids were identified as having acquired SalI, HpaI, and NsiI sites while still retaining the NotI and XhoI sites of the starting plasmid. One such recombinant plasmid with a 79 bp linker sequence was identified and designated pXN-4 (FIG. 5).

A similar approach was used to insert a 40 bp 3' linker between the XbaI and BamHI sites of pXN-4. The oligonucleotides used to synthesize the linker were PNT Xba (CGT TCT AGA ATA ACT TCG TAT AAT GTA TGC TAT; SEQ ID NO:5) and PNT Bam (CGT GGA TCC ATA ACT TCG TAT AGC ATA CAT TAT; SEQ ID NO:6). Plasmid pXN-4 and the double-stranded linker DNA were digested with XbaI and BamHI. The purified fragments were joined by DNA ligation and transformed into competent WM1100 *E. coli* bacteria. Plasmid DNA was digested with XbaI and BamHI, end-labelled with $^{32}$P-dCTP and Klenow polymerase, and resolved on an 8% acrylamide gel (Maniatis et al., 1982, supra). The gel was dried and exposed to X-ray film. Proper recombinant clones were identified by the presence of a 40 bp band liberated by the XbaI-BamHI double digest. The resulting plasmid was called pPNTlox$^2$ (FIG. 5) . This construct includes the $neo^r$ flanked by the loxP sequences; see Sauer, supra.

To confirm the sequences of the inserted linkers, a fragment containing both linkers was isolated from pPNTlox$^2$, using NotI and EcoRI, and cloned into pBlueScript® SK+, a vector more amenable to nucleotide sequencing. Identity of the linkers was confirmed by direct nucleotide sequencing (Sanger, *Proc. Natl. Acad. Sci. USA,* 74: 5463–5467, 1977) using T3 and T7 sequencing primers (Stratagene® Inc., La Jolla, Calif.).

Construction of the pSOD-TV Deletion Vector

Figure 6:
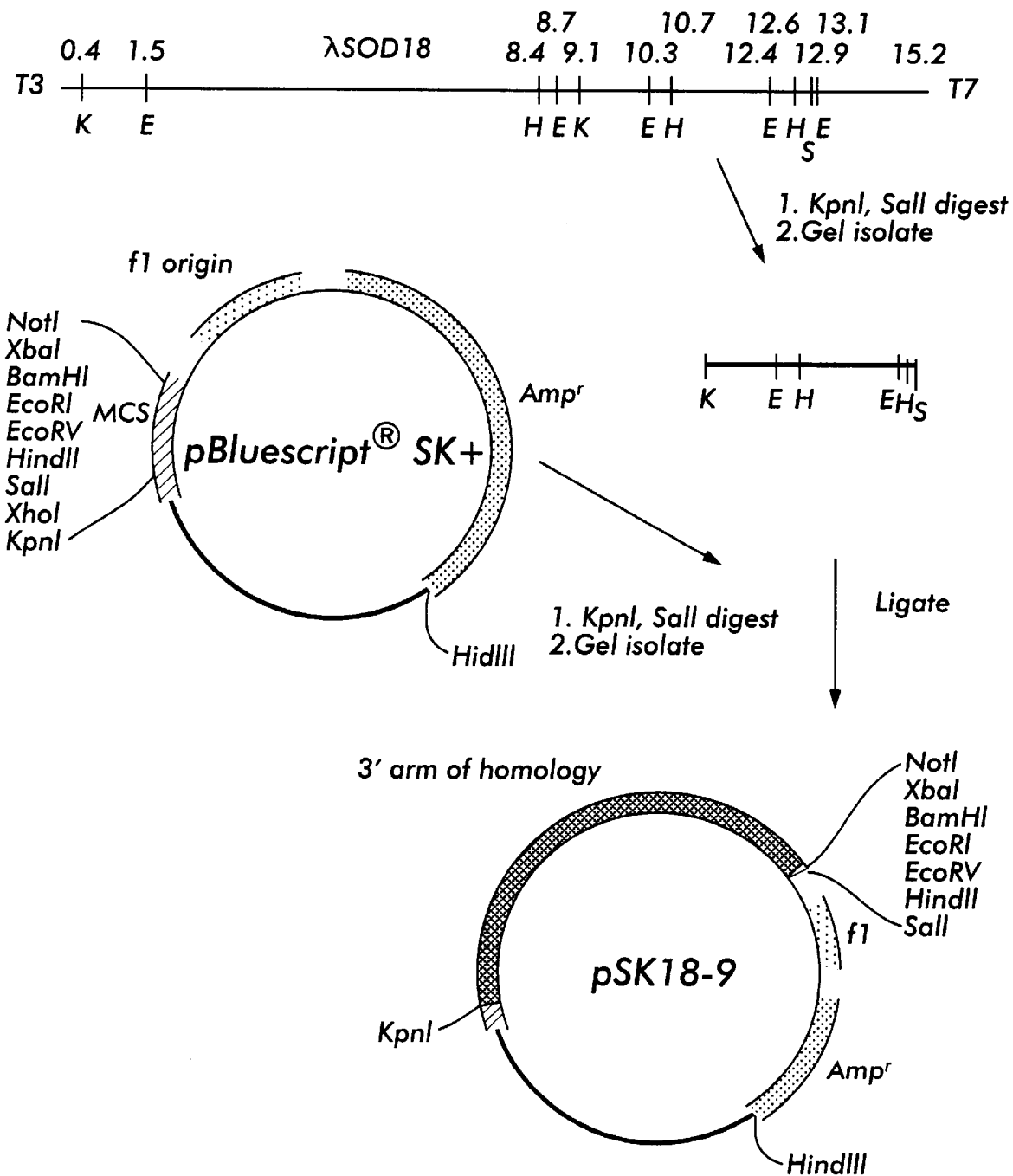
FIG. 6 depicts the construction of intermediate plasmid pSK18-9.

The deletion vector pSOD-TV was assembled by inserting the selected 5' and 3' arms of homology appropriately into pPNTlox$^2$. Initially, both arms of homology were subcloned from the phage inserts into pBlueScript® SK+. The map of λSOD18 (FIG. 2a) shows restriction enzymes sites for KpnI (K), EcoRI (E), HindIII (H), and SalI (S). The T3 and T7 promoters at either end of the cloned inserts are indicated. The 3' arm of homology was isolated from λSOD18 by digesting 10 μg of bacteriophage DNA with the enzymes KpnI and SalI, resolving the digested DNA on a 0.8% agarose gel, and purifying the excised 3.3 kb fragment with GeneClean® II (Bio 101 Inc., La Jolla, Calif.). The same digest and gel isolation procedure were performed in parallel with pBlueScript® SK+ DNA except that the purified band was 3.0 kb. Approximately 400 ng of the purified lambda DNA and 100 ng of the purified plasmid DNA were combined in a 10 μl ligation reaction. Following transformation of competent WM1100 *E. coli*, plasmid DNA was isolated from ampicillin-resistant bacteria and analyzed by restriction enzyme analysis to identify the resultant plasmid pSK18-9 (FIG. 6).

Figure 7:
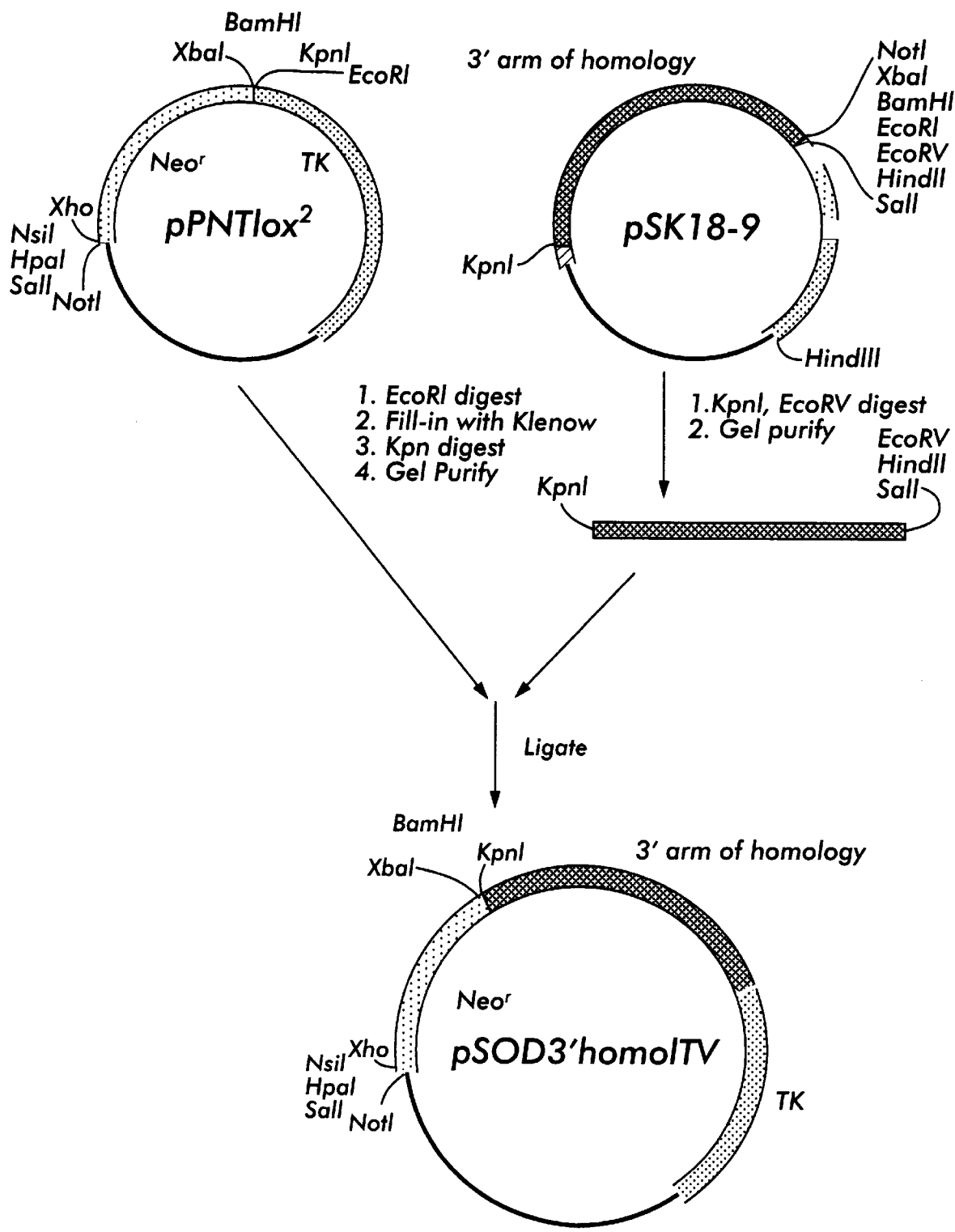
FIG. 7 depicts the construction of intermediate plasmid pSOD3'homolTV.

To clone the 3' arm of homology into pPNTlox$^2$ , the arm was liberated from pSK18-9 by enzymatic restriction with KpnI and EcoRV and purified by gel isolation. The plasmid pPNTlox$^2$ was digested with EcoRI and the resultant 4 base overhang was filled-in using Klenow polymerase (Maniatis et al., 1982, supra). Following further digestion with KpnI, the pPNTlox$^2$ plasmid DNA was gel purified and ligated to the purified 3' arm of homology. Following bacterial transformation, proper recombinants were identified by restriction enzyme analyses. The resulting plasmid was designated pSOD3'homolTV (FIG. 7).

Figure 8:
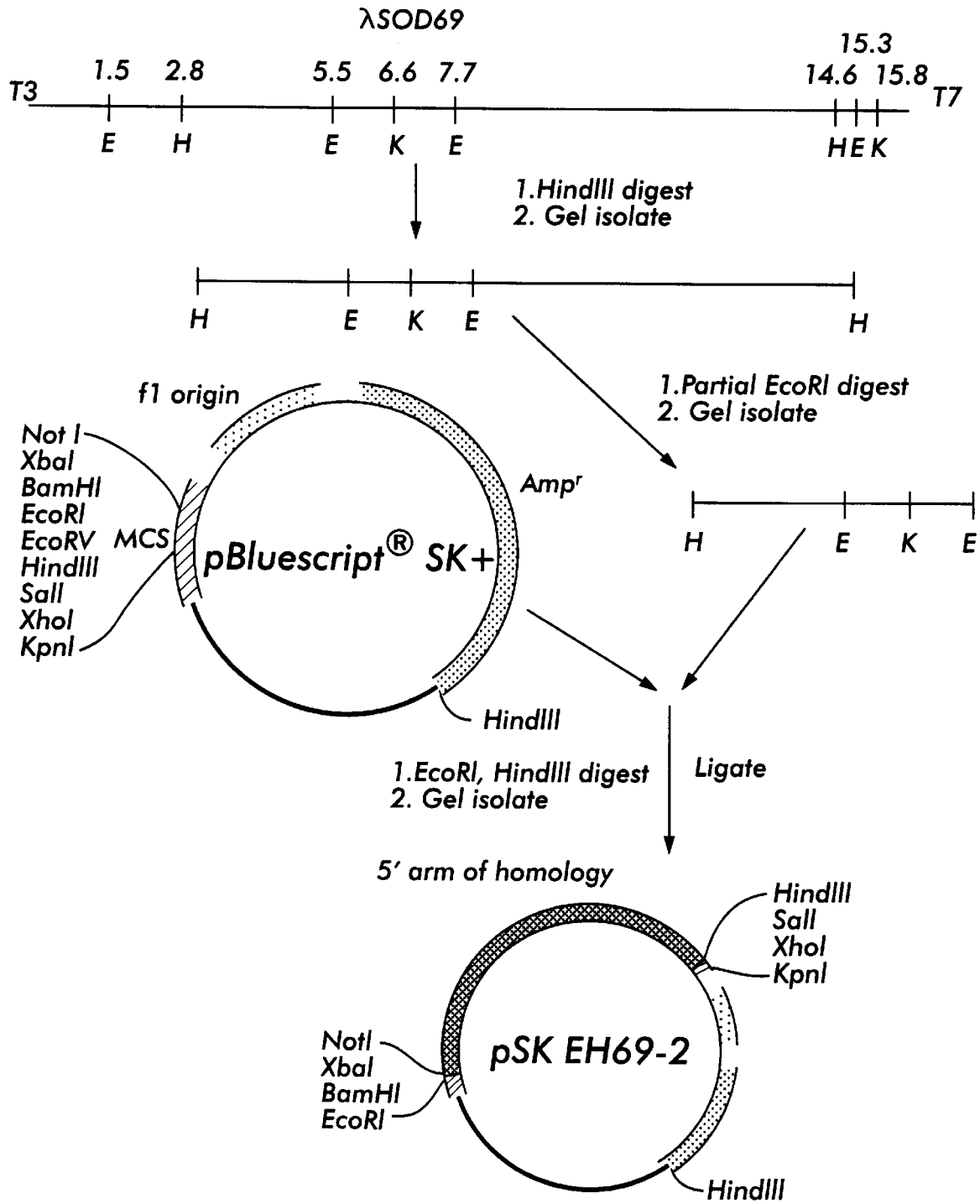
FIG. 8 depicts the construction of intermediate plasmid pSK EH69-2.

A similar approach was used to isolate, purify, and subclone the 5' arm of homology into pBlueScript® SK+. The map of λSOD69 (FIG. 2a) shows restriction enzyme sites for KpnI (K), EcoRI (E), and HindIII (H). The T3 and T7 promoters at either end of the cloned insert are indicated. The 5' arm was isolated from λSOD69 by first digesting the bacteriophage DNA with HindIII, isolating an 11.8 kb DNA fragment by gel electrophoresis, and then partially digesting this DNA fragment with limited amounts of EcoRI (1 U/μg) for 1 to 5 minutes. The reaction was stopped with 20 mM EDTA. A 4.9 kb DNA fragment was purified after agarose gel electrophoresis and cloned into the EcoRI and HindIII sites of pBlueScript® SK+ to generate pSK EH69-2 (FIG. 8).

Figure 9:
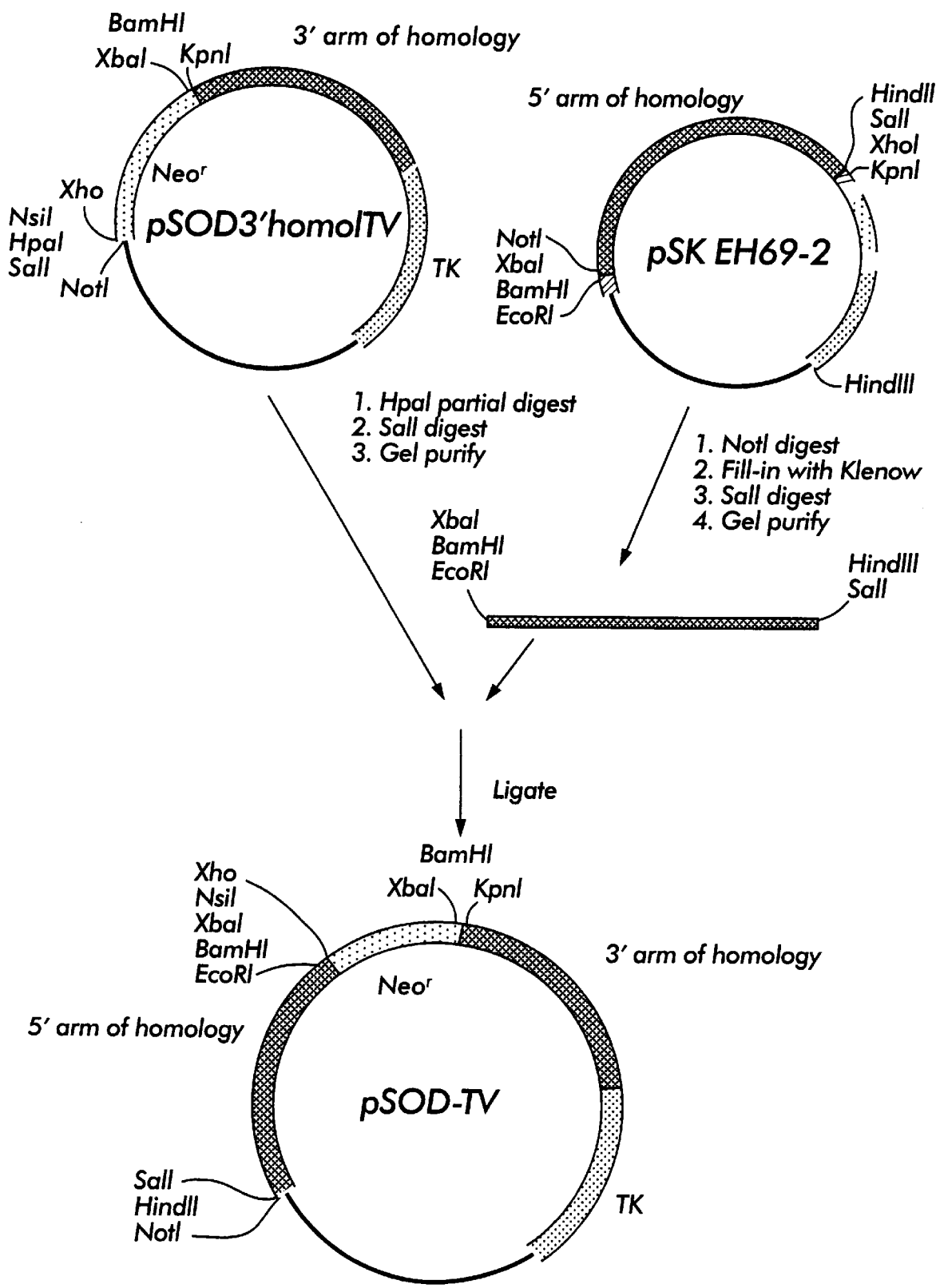
FIG. 9 depicts the construction of deletion vector pSOD-TV.

To construct plasmid pSOD-TV, the 5' arm of homology was removed from pSKEH69-2 by first digesting with NotI, filling-in the overhang with Klenow polymerase, and then digesting with SalI. In parallel, pSOD3'homolTV was first partially digested with HpaI, then completely digested with SalI. The final deletion vector pSOD-TV was constructed by ligation of the two gel-purified fragments (FIG. 9).

EXAMPLE 3

Deletion of the SOD-1 Gene in ES Cells

Cells: The R1 line of ES cells derived from 129/Sv×129/Sv-CP F1 hybrid mice (pigmented) (Nagy, et al., *Proc. Natl. Acad. Sci. USA*, 90: 8424–8428, 1993, incorporated herein by reference) was obtained from Dr. Janet Rossant, Dr. Andras Nagy, Reka Nagy, and Dr. Wanda Abramow-Newerly (Mt. Sinai Hospital, Toronto, Ontario, Canada). The cells were grown in ES cell medium consisting of Dulbecco's Modification of Eagle's Medium (Eagle's medium containing L-glutamine and 4500 mg/L glucose; Mediatech Inc., Herndon, Va.) supplemented with 20% fetal bovine serum (FBS; Hyclone Laboratories Inc., Logan, Utah; cat. #A-1115; Lot #11152154), 0.1 mM non-essential amino acids (Mediatech 25025-L1), 2 mM L-glutamine (Mediatech 25-005-L1), $10^{-6}$M β-mercaptoethanol (Gibco 21985-023), 1 mM sodium pyruvate (Mediatech 25-000-L1), 1× concentration of a penicillin (50 IU/ml) streptomycin (50 mcg/ml) solution (Mediatech 30-001-L1), and 1000 U/ml of leukemia inhibitory factor (Gibco BRL 13275-029). The cells were grown on tissue culture plastic that had been briefly treated with a solution of 0.1% gelatin (Sigma G9391), i.e., gelatinized plates.

The cultures were plated at 1×10$^5$ cells per ml in 100 mm×15 mm plastic culture plates and passaged every 48 hours, or when the cells became about 80% confluent. For passage, the cells were first washed with phosphate buffered saline without Ca$^{2+}$ and Mg$^{2+}$, hereinafter referred to as "PBS", and then treated with a trypsin/EDTA solution (0.05% trypsin, 0.02% EDTA in PBS). After all of the cells were in suspension, the trypsin digestion was stopped by the addition of ES cell medium. The cells were collected by centrifugation, resuspended in 5 ml of ES cell medium, and a 1 ml aliquot of the cell suspension was used to start a new plate of the same size.

DNA Gene-Targeting of ES cells: pSOD-TV DNA (400 μg) was prepared for electroporation by digesting it with Not I in a 1 ml reaction volume. The DNA was then precipitated by the addition of ethanol, washed with 70% ethanol, and resuspended in 500 μl of sterile water.

The NotI-linearized pSOD-TV DNA was electroporated into ES cells using a Bio-Rad Gene Pulser® System (Bio-Rad Laboratories, Hercules, Calif.) as follows. In each of 10 electroporation cuvettes, 40 μg of DNA was electroporated into 5×10$^6$ cells suspended in 0.8 ml ES cell medium. The electroporation conditions were 250 V and 500 μF which typically result in time constants ranging between 5.7–6.2 seconds. After electroporation the cells were incubated for 20 minutes at room temperature in the electroporation cuvettes. All the electroporated cells were then pooled and distributed approximately equally onto 20 gelatinized plates (100 mm×15 mm).

After 24 hours, the plates were aspirated and fresh ES cell medium was added. The following day, the medium in 19 plates was replaced with ES cell medium supplemented with 150 μg/mL of G418 (Gibco) and 0.2 μM ganciclovir (Syntex, Palo Alto, Calif.). The medium in one plate was supplemented with 150 μg/mL of G418 alone. After an additional 6 days, resultant individual ES cell colonies were picked off of the plates and separately expanded in individual wells of 24 well plates as described by Wurst et al., *Gene Targeting* Vol. 126, Edited by A. L. Joyner, IRL Press, Oxford University Press, Oxford, England, pp. 33–61, 1993, incorporated herein by reference. A comparison of the number of colonies that grew on the plates supplemented with G418 and ganciclovir versus the number that grew on the plates supplemented G418 alone was used to determine the efficiency of negative selection, which was 3.2 fold.

Analyses of the gene-targeted ES cells: When the cell culture in each well of the 24-well plates became approximately 80% confluent, the cells were washed with PBS and then dispersed with two drops of trypsin-EDTA. Trypsinization was stopped by the addition of 1 ml of ES cell medium. An aliquot (0.5 mL) of this suspension was transferred to each of two wells of separate 24-well plates. After the cells had grown to near confluence, one of the plates was used for cryopreservation of the cell line while the other was used as a source of DNA for each of the cloned cell lines.

For cryopreservation, the cells in a 24-well plate were first chilled by placing the plate on ice. The medium was then replaced with fresh ES cell medium supplemented with 10% DMSO and 25% FBS. The plate was then cooled at approximately 0.5° C. minute by insulating the plate in a styrofoam box and placing it in a –70° C. freezer.

To isolate the DNA from the cloned cell lines on the other 24-well plate, the medium in each well was replaced with 500 μl of digestion buffer (100 mM Tris-HCl, pH8.5, 5 mM EDTA, 0.2% SDS, 200 mM NaCl, 100 μg/ml proteinase K) and incubated overnight at 37° C. After overnight incubation, 500 μl of isopropanol was added to each well and the plate was agitated for 15 minutes on an orbital shaker. The supernatant fluid was aspirated and replaced with 500 μl of 70% ethanol and the plate was shaken for an additional 15 minutes. The DNA precipitate was picked out of the well and dissolved in 50 μl of TE solution (10 mM Tris-HCl pH 7.5, 1 mM EDTA).

The primary analysis for deletion of the SOD-1 gene involved a Southern hybridization screen of ApaI digested ES cell DNA. The probe for this analysis was derived from the 5' end of the SOD gene outside of the 5' arm of homology (FIG. 10a). An aliquot (10 μl) of each DNA sample was digested with ApaI, resolved on a 0.8% agarose gel, and transferred to a GeneScreen Plus® membrane. The probe was prepared by first isolating the 1.3 kb EcoRI-HindIII fragment from λSOD69 (FIG. 2a). Subsequent AluI digest of this fragment yielded the 600 base pair probe. The probe was labelled with $^{32}$P-dCTP by random priming and hybridized overnight to the membrane at 58° C. (Church et al., Proc. Natl. Acad. Sci. USA, 81: 1991–1995, 1984). An ES cell line in which the SOD-1 gene has been successfully deleted yields 9 kb and 10 kb ApaI fragments, in this assay (FIG. 10). The targeting event replaces all of the SOD-1 coding sequence and introns with the neo$^r$ positive selection marker. A normal SOD-1 gene carries an ApaI site located approximately 1.0 kb downstream from the 5' border of the region to be deleted. The neo$^r$ marker which replaces the SOD-1 gene carries with it an ApaI site near its 5' end. As a result, this assay yields a 10 kb ApaI fragment from the normal SOD-1 gene and a 9 kb ApaI fragment from the deleted SOD-1 gene.

All cell lines scored as putative homologous recombinants by the primary screen were then further screened using a 1.8 kb EcoRI probe (isolated from an λSOD69, EcoRI digest) on SpeI digested ES cell DNA. In this case, the normal SOD-1 gene yielded a 9 kb fragment and the mutant SOD-1 gene a 10 kb fragment (FIG. 10.) From 80 cell lines (numbered 1–80) whose DNA was analyzed, five were identified as having undergone proper homologous recombination. Three of the five cell lines that were identified as having undergone proper homologous recombination by both screens were then thawed and their cell numbers expanded. Cells from the resulting cultures were used to make chimeric mice.

EXAMPLE 4

Establishment of SOD-1 Null Mice

SOD-1 gene-targeted ES cells were used to make chimeric mice by aggregating the ES cells to E2.5 embryos and transferring the aggregated embryos to pseudopregnant females. (Wood et al., Nature, 365: 87–89, 1993, incorporated herein by reference). ES cells were prepared for aggregation by limited trypsinization to produce clumps that averaged 10–15 cells. E2.5 embryos were collected from superovulated CD-1 female mice (albino) by oviduct flushing as described by Hogan et al., Manipulating the Mouse Embryo: A Laboratory Manual, Cold Spring Harbor Laboratory, Cold Spring Harbor, N.Y., 1986). The zona pellucida was removed from the embryos using acidic Tyrode's solution (Sigma Chemical Co., St. Louis, Mo.). Aggregation wells were created by pressing a blunt metal instrument i.e., a darning needle into tissue culture plastic. Embryos were then placed in a well together with a clump of approximately 10–15 ES cells in a small drop (approximately 20 µl) of M16 medium (Sigma Chemical Co., St. Louis, Mo.) under mineral oil. After an overnight incubation (37° C., 100% humidity, 5% $CO_2$ in air), approximately 20 of the aggregated embryos were transferred to the uterine horns of each pseudopregnant female (Hogan et al., supra). Contribution of the ES cells to the offspring was scored by the appearance of pigmented coat color. Pigmented mice were termed chimeric founders. Germline contribution by the ES cells was scored by the appearance of pigmented offspring from a cross between the chimeric founders and CD-1 females.

Three of the five gene-targeted ES cell lines were used in embryo aggregations. One (line 42) gave five germline chimeras, another (line 58) gave four germline chimeras, and the third (line 66) gave none (See Table 1).

TABLE 1

| Cell Line Number | Number of Embryo Aggregations | Number of Pups Born | Number of Chimeric Founders | Number of Germline Chimeras |
| --- | --- | --- | --- | --- |
| 42 | 138 | 31 | 18 | 5 |
| 58 | 130 | 24 | 14 | 4 |
| 66 | 141 | 33 | 3 | 0 |

The germline chimeras were then used to establish lines of SOD-1 deficient mice and mice lacking SOD-1. The presence of the gene-targeted SOD-1 allele in the pigmented offspring was determined using the Southern blot strategy described above with genomic DNA prepared from a tail sample (Hogan et al., supra). Heterozygous SOD-1 null mice have 9 kb and 10 kb ApaI fragments that hybridize with the 5' AluI SOD probe. Homozygous SOD-1 null mice were established by crossing 2 heterozygous SOD-1 null mice and were identified as having only a 9 kb ApaI genomic DNA fragment that hybridized with the 5' AluI SOD probe.

EXAMPLE 5

Cu/Zn SOD Protein Levels and Enzymatic Activity in the SOD-1 Null Mice

To confirm that the targeted disruption of the SOD-1 locus results in a reduction of Cu/Zn SOD levels in the tissues of the resulting mammals, blood samples were collected from wild-type mice, and mice shown to be heterozygous and homozygous for the SOD-1 gene. The blood samples were analyzed for Cu/Zn SOD protein by immunoblot analysis. Red blood cell lysates were prepared by lysing the blood cells (approximately 75 ul) by several cycles of alternately freezing and thawing. The protein concentrations of the cell lysates were determined using the BCA method (Pierce, Rockville, Ill.). An aliquot (2 to 2.5 µg of protein) of each sample was electrophoresed on a 4–20% polyacrylamide gel (Novex, San Diego, Calif.) using a Tris/glycine/SDS (25 mM Tris/192 mM glycine/0.1% SDS) buffer system.

The separated proteins were transferred to nitrocellulose filters by electroelution and the resulting filters were blocked by incubation in blotto solution—5% non-fat, dry milk in 25 mM Tris-buffered saline (1× TBS)—for 30 minutes. The filters were then submersed in a primary antibody solution (1:10,000 dilution in blotto solution) and incubated for between 2 and 18 hours. The primary antibody used was polyclonal rabbit antisera raised against purified mouse Cu/Zn SOD protein produced in E. coli (Hazelton Research Products, Denver, Pa.). The filters were washed three times for 5 minutes each in 1× TBS and incubated in secondary antibody solution (1:2,000 dilution in blotto solution) for two hours. The secondary antibody was a goat anti-rabbit IgG conjugated to alkaline phosphatase (Bio-Rad, Richmond, Calif.). The filters were washed three times for 5 minutes each in 1× TBS and stained for alkaline phosphatase activity by incubating them for between 5 and 60 minutes in a commercially available alkaline phosphatase detection reagent (Bio-Rad, Richmond, Calif.).

Stained bands corresponding to Cu/Zn SOD protein were quantitated using a DocuGel V image analysis system and RFLPscan software (Scanalytics, Billerica, Mass.). The levels of Cu/Zn SOD protein are depicted in FIG. 11 (solid bars) and are expressed relative to the level of Cu/Zn SOD protein in the samples from wild-type mammals. The results of these studies indicate that the heterozygous SOD-1 null mice exhibit an expected near 50% reduction in Cu/Zn SOD protein. Further, the homozygous SOD-1 null mammals showed no detectable Cu/Zn SOD protein on Western blots.

Cu/Zn SOD enzymatic activity in the red blood cell lysates was measured using the NADPH oxidation method of Paoletti, et al. (*Anal. Biochem.,* 154:536–541, 1986, incorporated herein by reference). Protein samples (1 mg) from the wild-type, heterozygous SOD-1 null mice, and homozygous SOD-1 null mice were extracted with an equal volume of ethanol:chloroform (2:1) and the resulting supernatant fluid was dialyzed overnight against PBS saline at 4° C. The protein concentration of the dialysate was determined using the BCA method (Pierce, Rockville, Ill.) and 10 ug of each sample was assayed for SOD activity. Enzymatic activity was expressed relative to the wild-type control sample (FIG. 11, cross-hatched bars). The Cu/Zn SOD activity of the sample from heterozygous SOD-1 null mammals was approximately 50% of that displayed by samples from the wild-type mammals, consistent with the expectation that only one SOD-1 allele was active in the heterozygous mammals. Furthermore, the protein sample derived from the homozygous SOD-1 null mice showed nearly a total reduction in Cu/Zn SOD activity. The small residual activity detected in this assay likely represents background activity associated with the assay, but could also reflect an endogenous superoxide scavenging activity supplied by an alternate protein.

EXAMPLE 6

Maintenance Conditions of SOD-1 Null Mice

Young adult heterozygous and homozygous SOD-1 null mice are currently being maintained under viral and antigen free conditions as defined by Charles River Laboratories, Wilmington, Mass. Presently, the diet for these mice is the same as that provided to laboratory mice. No other unique or distinguishing living conditions have thus far been required for the mice.

Attempts at the breeding of homozygote males with homozygote females have been unsuccessful thus far, which we believe is due to the deficiency of Cu/Zn SOD and the oxidative stress occasioned by pregnancy. The homozygote breeding pairs are capable of conceiving offspring, but the litters have been small in number (1–2) and the pups are either still-born, or those pups which are born alive die almost immediately.

The colony can be propagated by the breeding of heterozygous SOD-1 null males and females, homozygous SOD-1 null males to either wild type or heterozygous SOD-1 null females, or wild type males to homozygous SOD-1 null females.

While the invention has been described and illustrated with respect to specific embodiments, it is to be understood that modifications and equivalents apparent to those skilled in the art are intended to be within the scope of the disclosure and the following claims.

All references referred to herein are hereby incorporated by reference.

What is claimed is:

1. A homozygous SOD-1 null mouse whose somatic and germ cells lack both SOD-1 alleles, said mouse prepared from an embryonic stem cell lacking at least one SOD-1 allelle following modification of said embryonic stem cell by homologous recombination, wherein said homozygous SOD-1 null mouse reaches sexual maturity and is able to propagate.

2. A homozygous SOD-1 null offspring mouse prepared from the propagation of the mouse of claim 1 with a mouse whose somatic and germ cells comprise at least one SOD-1 allelle, wherein said offspring mouse reaches sexual maturity and is able to propagate.

3. The homozygous SOD-1 null mouse of claim 1 wherein no measurable amount of Cu/Zn SOD is produced by said mouse.

4. A method for determining the effectiveness of a compound for counteracting the deleterious effects of oxidative stress comprising:

a) simultaneously exposing to oxidative stress (1) at least one treatment mouse, said mouse being a first homozygous SOD-1 null mouse of claim 1, and (2) at least one control mouse, said mouse being a second homozygous SOD-1 null mouse of claim 1;

b) administering said compound to said at least one treatment mouse of step (a)(1); and c) determining if said compound is effective in counteracting the deleterious effects of said oxidative stress by comparing the effects of said stress on said at least one control mouse of step (a)(2) with the effects of such stress on said at least one treatment mouse of step (a)(1).

* * * * *

UNITED STATES PATENT AND TRADEMARK OFFICE
CERTIFICATE OF CORRECTION

PATENT NO. : 5,814,300     Page 1 of 2

DATED : Scott et al.

INVENTOR(S) :
September 29, 1998

It is certified that error appears in the above-identified patent and that said Letters Patent is hereby corrected as shown below:

On the cover page, first column, [56] "OTHER PUBLICATIONS", please delete "Huanh" and insert --Huang-- therefor.

On page 2, second column, under "OTHER PUBLICATIONS", at "Sanchez-Ramos et al.", second and third lines thereof, please delete "*Neurodegen.*, : 197-204, 1994." and insert --*Neurodegen.*, 3: 197-204, 1994.-- therefor.

In column 1, line 14, please delete "($O_2^{--}$)" and insert --($O_2^{\cdot -}$) therefor.

In column 1, line 17, please delete "($O_2^{--}$)" and insert --($O_2^{\cdot -}$) therefor.

In column 1, line 49, please delete "The human Cu/Zn SOD has 153 amino acids per".

In column 1, line 50, please insert (as a new paragraph) --The human Cu/Zn SOD has 153 amino acids per--.

UNITED STATES PATENT AND TRADEMARK OFFICE
CERTIFICATE OF CORRECTION

PATENT NO. : 5,814,300
DATED : September 29, 1998
INVENTOR(S) : Scott et al.

It is certified that error appears in the above-identified patent and that said Letters Patent is hereby corrected as shown below:

In column 5, line 4, please delete "Cu/ZN SOD" and insert --Cu/Zn SOD-- therefor.

In column 10, line 6, please delete "PPNT DNA" and insert --pPNT DNA-- therefor.

In column 11, line 47, please delete "(Mediatech 25025-L1)" and insert --(Mediatech 25-025-L1)-- therefor.

Signed and Sealed this

Eighth Day of June, 1999

Attest:

Q. TODD DICKINSON

*Attesting Officer*     Acting Commissioner of Patents and Trademarks